(12) United States Patent
Fogarty et al.

(10) Patent No.: US 11,266,801 B2
(45) Date of Patent: Mar. 8, 2022

(54) VENTILATION DEVICES AND SYSTEMS AND METHODS OF USING SAME

(71) Applicant: University of Utah Research Foundation, Salt Lake City, UT (US)

(72) Inventors: Michael Fogarty, Provo, UT (US); Joseph Orr, Park City, UT (US); Kai Kuck, Park City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 201 days.

(21) Appl. No.: 15/767,094

(22) PCT Filed: Oct. 7, 2016

(86) PCT No.: PCT/US2016/055946
§ 371 (c)(1),
(2) Date: Apr. 9, 2018

(87) PCT Pub. No.: WO2017/062742
PCT Pub. Date: Apr. 13, 2017

(65) Prior Publication Data
US 2019/0070374 A1    Mar. 7, 2019

Related U.S. Application Data

(60) Provisional application No. 62/239,593, filed on Oct. 9, 2015.

(51) Int. Cl.
*A61M 16/00* (2006.01)
*A61M 16/06* (2006.01)
(Continued)

(52) U.S. Cl.
CPC ...... *A61M 16/024* (2017.08); *A61M 16/0003* (2014.02); *A61M 16/0051* (2013.01);
(Continued)

(58) Field of Classification Search
CPC .............. A61M 16/021; A61M 16/022; A61M 16/024; A61M 16/026; A61M 16/0066;
(Continued)

(56) References Cited

U.S. PATENT DOCUMENTS 4,297,999 A * 11/1981 Kitrell ................. A61M 16/021
128/205.16
5,365,922 A * 11/1994 Raemer ................ A61B 5/0833
128/202.22
(Continued)

FOREIGN PATENT DOCUMENTS

WO   WO2008025079   3/2008

OTHER PUBLICATIONS

"High Flow Calculations," Web page <https://rtmouthbreather.files.wordpress.com/2009/11/high-flow-formulas.pdf>, 16 pages, Nov. 14, 2014, retrieved from Internet Archive Wayback Machine <https://web.archive.org/web/2014*/https://rtmouthbreather.files.wordpress.com/2009/11 . . . > on Aug. 3, 2020. (Year: 2014).*

*Primary Examiner* — Kendra D Carter
*Assistant Examiner* — Thomas W Greig
(74) *Attorney, Agent, or Firm* — Thorpe North & Western

(57) ABSTRACT

A ventilation system having a mask, a blowing assembly, and a processor. The mask has a mask body and a pressure sensor operatively associated with the mask body and configured to measure pressure within the mask. The mask body defines an inlet opening and a plurality of leak openings. The blowing assembly is positioned in fluid communication with the inlet opening of the mask body and configured to direct air to the inlet opening of the mask body. The processor is positioned in operative communication with the blowing assembly and the pressure sensor of the mask. The processor is configured to selectively control the blowing assembly based upon at least the measured pressure within the mask.

24 Claims, 9 Drawing Sheets

(51) Int. Cl.
*A61M 16/01* (2006.01)
*A61M 16/12* (2006.01)

(52) U.S. Cl.
CPC ........ *A61M 16/0069* (2014.02); *A61M 16/06* (2013.01); *A61M 16/0084* (2014.02); *A61M 16/01* (2013.01); *A61M 16/12* (2013.01); *A61M 2016/0027* (2013.01); *A61M 2016/0033* (2013.01); *A61M 2202/0208* (2013.01); *A61M 2205/15* (2013.01); *A61M 2205/50* (2013.01); *A61M 2205/505* (2013.01); *A61M 2230/42* (2013.01)

(58) Field of Classification Search
CPC .......... A61M 16/0069; A61M 16/0051; A61M 2016/0003; A61M 2016/0015; A61M 2016/003; A61M 2016/0033; A61M 2016/0036; A61M 16/06–0694
See application file for complete search history.

(56) References Cited

U.S. PATENT DOCUMENTS

| | | | |
|---|---|---|---|
| 5,551,419 A * | 9/1996 | Froehlich | A61M 16/024 128/204.23 |
| 6,152,129 A | 11/2000 | Berthon-Jones | |
| 6,581,595 B1 * | 6/2003 | Murdock | A61B 5/083 128/204.18 |
| 7,047,971 B2 * | 5/2006 | Ho | A61M 16/06 128/206.21 |
| 7,370,650 B2 * | 5/2008 | Nadjafizadeh | A61M 16/024 128/204.18 |
| 7,726,314 B1 * | 6/2010 | Ming | A61M 16/208 128/206.12 |
| 2005/0103343 A1 * | 5/2005 | Gosweiler | A62B 18/006 128/206.12 |
| 2009/0205662 A1 * | 8/2009 | Kwok | A61M 16/0069 128/204.23 |
| 2012/0289851 A1 * | 11/2012 | Varga | A61B 5/0836 600/532 |
| 2013/0213401 A1 * | 8/2013 | Haibach | A61M 16/0633 128/205.25 |
| 2014/0007878 A1 * | 1/2014 | Armitstead | A61M 16/0069 128/204.23 |
| 2015/0128942 A1 * | 5/2015 | Tatkov | A61M 16/0003 128/203.14 |
| 2015/0165140 A1 * | 6/2015 | Cappelli | A61M 16/0051 128/204.21 |
| 2015/0217075 A1 * | 8/2015 | Nair | A61B 1/01 600/531 |
| 2017/0189635 A1 * | 7/2017 | Beard | A61M 16/0841 |
| 2020/0324150 A1 * | 10/2020 | Nelson | A61M 16/20 |

* cited by examiner

VENTILATION DEVICES AND SYSTEMS AND METHODS OF USING SAME

CROSS-REFERENCE TO RELATED APPLICATIONS

This application claims priority to International Patent Application Number PCT/US2016/055946 filed on Oct. 7, 2016, which application claims the benefit of U.S. Provisional Patent Application No. 62/239,593, filed Oct. 9, 2015, each of which are hereby incorporated herein by reference in their entireties.

GOVERNMENT SUPPORT

This invention was made with government support under Grant Number NNX09A073A awarded by the National Aeronautics and Space Administration. The government has certain rights in the invention.

FIELD

This disclosure relates to portable ventilation devices and systems that provide leak-adaptable ventilation and monitoring.

BACKGROUND

Many spontaneously breathing patients that are sedated or anesthetized experience significant respiratory complications, including apneic events. If not addressed, these respiratory complications can and do lead to serious and life-threatening situations. The typical approach in these cases is to manually ventilate the patients using a face mask and a bag, as shown in FIGS. 1 and 2. This approach requires a great deal of skill, at least two hands, and distracts the clinician from more important tasks.

Thus, there is a need for a noninvasive ventilation device that provides just enough gentle respiratory support to prevent obstruction of the airways during sedation and anesthesia. For example, there is a need for a device that can monitor respiratory rate and tidal volume, deliver oxygen, and be capable of automatically increasing the level of respiratory support while providing appropriate warnings to a clinician. Some of these features can be found in advanced critical care ventilators, but current critical care ventilators are expensive and bulky. Therefore, there is a further need for a ventilator that is small and portable, does not need compressed gases, and can operate for an extended period of time without connection to a wall power source. As further disclosed herein, there is a further need for ventilation devices and systems that can make the support and the monitoring of a patient robust and reliable, even during large or varying leaks around the patient's face mask.

SUMMARY

Disclosed herein, in one aspect, is a ventilation system having a mask, a blowing (pressure generating) assembly, and a processor. The mask can include a mask body having an inner surface configured for engagement with a face of a subject and an opposed outer surface. The mask can further include a pressure sensor operatively associated with the mask body and configured to measure pressure within the mask. The mask body can define an inlet opening and a plurality of leak openings extending between the inner and outer surfaces of the mask body. The blowing assembly can be positioned in fluid communication with the inlet opening of the mask body and configured to direct air to the inlet opening of the mask. The processor can be positioned in operative communication with the blowing assembly and the pressure sensor of the mask. In operation, the processor can be configured to selectively control the blowing assembly based upon at least the measured pressure within the mask.

As further disclosed herein, the ventilation system can further comprise one or more flow sensors for measuring the flow of air and/or oxygen into the mask. In operation, the processor can be configured to determine the rate at which air/oxygen enters the mask, the rate at which air/oxygen exits the mask through the leak openings, and the rate at which air/oxygen is inhaled by a subject. The ventilation system can provide appropriate ventilation assistance based upon the determined rate of air/oxygen being inhaled by the subject. Thus, as further disclosed herein, the ventilation system is adaptable to varying leak conditions.

Methods of using the disclosed ventilation system are also described.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein.

DETAILED DESCRIPTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a", "an", and "the" include plural referents unless the context clearly dictates otherwise. For example, use of the term "a leak opening" can refer to one or more of such leak openings unless the context indicates otherwise.

All technical and scientific terms used herein have the same meaning as commonly understood to one of ordinary skill in the art to which this invention belongs unless clearly indicated otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

Figure 11:
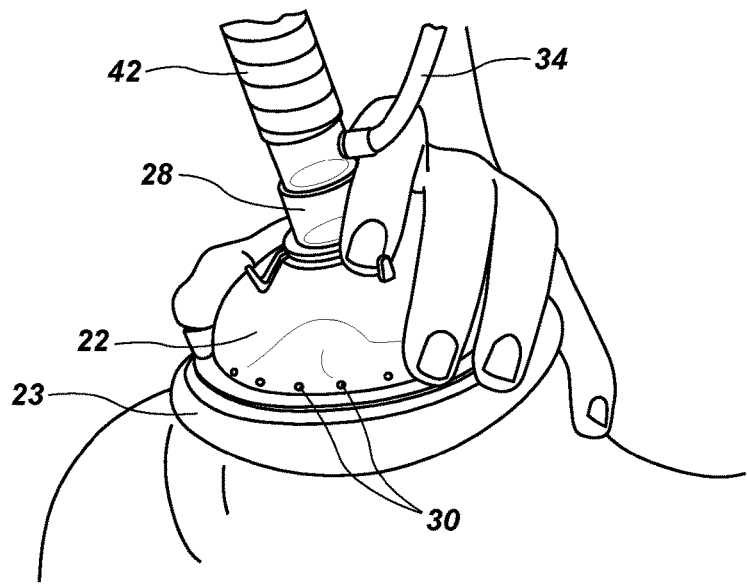
FIG. 11 is an image of another exemplary embodiment of a ventilation system as disclosed herein.

Disclosed herein with reference to FIGS. 3-5 and 10-13 is a ventilation system 10 comprising a mask 20, a blowing assembly 40, and a processor 60. In exemplary aspects, the mask 20 can comprise a mask body 22 and a pressure sensor 32 operatively associated with the mask body. In these aspects, the mask body 22 can have an inner surface 24 configured for engagement with a face 102 of a subject 100 and an opposed outer surface 26. Alternatively, in optional exemplary aspects, the mask 20 can comprise a mask cushion 23 that can extend along and underneath at least a portion of the periphery of the mask body 22 such that the mask cushion can be configured for engagement with the face 102 of the subject 100 to provide a comfortable fit over the mouth and nose of a subject. In further exemplary aspects, it is contemplated that the mask 20 can comprise any materials conventionally used for ventilation masks as are known in the art. Thus, the specific materials of the mask are not disclosed in detail herein. In operation, the pressure sensor 32 of the mask 20 can be configured to measure pressure within the mask. In exemplary aspects, the pressure sensor 32 can be positioned external to the mask 20 and placed in fluid communication with the mask via a tube or other conduit 34 that is in fluid communication with both the pressure sensor and the interior of the mask. Optionally, the tube 34 can be connected directly to the mask 20. Alternatively, as shown in FIG. 11, the tube 34 can be connected to other connection tubing, such as an inlet opening 28 as further disclosed herein, that is positioned in fluid communication with the mask 20. Optionally, in some aspects, it is contemplated that the pressure sensor 32 can be positioned within a housing of a ventilator assembly, which can also house the blowing assembly 40. In various optional aspects, when a tube 34 is used to provide fluid communication between the pressure sensor 32 and the mask 20, it is contemplated that the tube can be connected to the mask body 22 at a center portion of the mask corresponding to a location overlying the nose of the subject.

In another aspect, the mask body 22 can define an inlet opening 28 and a plurality of leak openings 30 extending between the inner and outer surfaces 24, 26 of the mask body 22. In further aspects, the blowing assembly 40 can be positioned in fluid communication with the inlet opening 28 of the mask body 22 and configured to direct air to the inlet opening of the mask 20. Optionally, in these aspects, it is contemplated that the blowing assembly 40 can be configured to deliver air to the inlet opening 28 of the mask body 22 (for example, through a tube or conduit 42) at a pressure of up to about 25 cm $H_2O$. In additional aspects, the processor 60 can be positioned in operative communication with (e.g., communicatively coupled to, by either wireless or wired connection) the blowing assembly 40 and the pressure sensor 32 of the mask 20. In operation, the processor 60 can be configured to selectively control the blowing assembly 40 based upon at least the measured pressure within the mask 20 (detected by pressure sensor 32).

In further exemplary aspects, the plurality of leak openings 30 can comprise any number and arrangement of leak openings sufficient to avoid blockage of all leak openings during handling of the mask 20, as further disclosed herein. Thus, in use, at least some of the leak openings will not be covered by the hands or other portions of the individuals handling the mask. It is contemplated that the number of leak openings 30 can vary based on the size of the mask body 22. Optionally, in some exemplary aspects, the number of leak openings can range from about 20 to about 25 depending on the size of the mask body 22. In another exemplary aspect, it is contemplated that the size of the leak openings 30 can vary so long as the leak openings are large enough to allow for expiration without the need for excessive exerted pressure and small enough to allow buildup of sufficient pressure during inspiration and constant flow (CPAP). Optionally, for example, the leak openings 30 can have a size in at least one dimension (e.g., a single dimension or a plurality of dimensions) ranging from about 1 to about 3 mm.

Optionally, in exemplary aspects, it is contemplated that the plurality of leak openings 30 of the mask 20 can be spaced about peripheral portions of the mask. Optionally, in these aspects, the leak openings 30 can be spaced evenly or substantially evenly about at least a portion of the periphery of the mask 20. In exemplary aspects, it is contemplated that the plurality of leak openings can be spaced radially inwardly from a peripheral edge of the mask (optionally, corresponding to the mask cushion 23) by a distance ranging from about 1 mm to about 5 mm. In further exemplary aspects, it is contemplated that the spacing of the leak openings 30 can be determined based on the size of the mask body 22 (e.g., the circumference of the mask body 22) and the number of leak openings. In further exemplary aspects, it is contemplated that the plurality of leak openings 30 can be positioned such that the leak openings cannot be fully blocked when the mask 20 is held as further disclosed herein. In further exemplary aspects, it is contemplated that the plurality of leak openings 30 can be positioned such that noise associated with the air flowing through the leak openings 30 is reduced. In still further exemplary aspects, it is contemplated that the leak openings 30 can be positioned such that the effective re-breathing deadspace in the mask 20 is minimized. In these exemplary aspects, it is contemplated that computational fluid dynamics can be used to position the leak openings 30 to optimize minimization of the deadspace. In even further exemplary aspects, it is contemplated that the leak openings 30 can be positioned such that air flow into the subject's eyes is minimized or eliminated. For example, it is contemplated that the plurality of leak openings 30 can be evenly spaced from one another about the periphery of the mask, with the exception of the two areas below the respective eyes of a subject, where the mask can be void of leak openings to prevent air from blowing directly into the eyes of the subject. These two void areas can each correspond to about 7 to about 10 percent of the total circumference (perimeter) of the mask body 22.

In some aspects, the processor 60 can be configured to generate a pressure alarm in response to the measured pressure in the mask 20 (measured by pressure sensor 32) falling below a predetermined value. In other aspects, the processor 60 can be configured to selectively activate the blowing assembly 40 to maintain a desired pressure within the mask 20.

Figure 3:
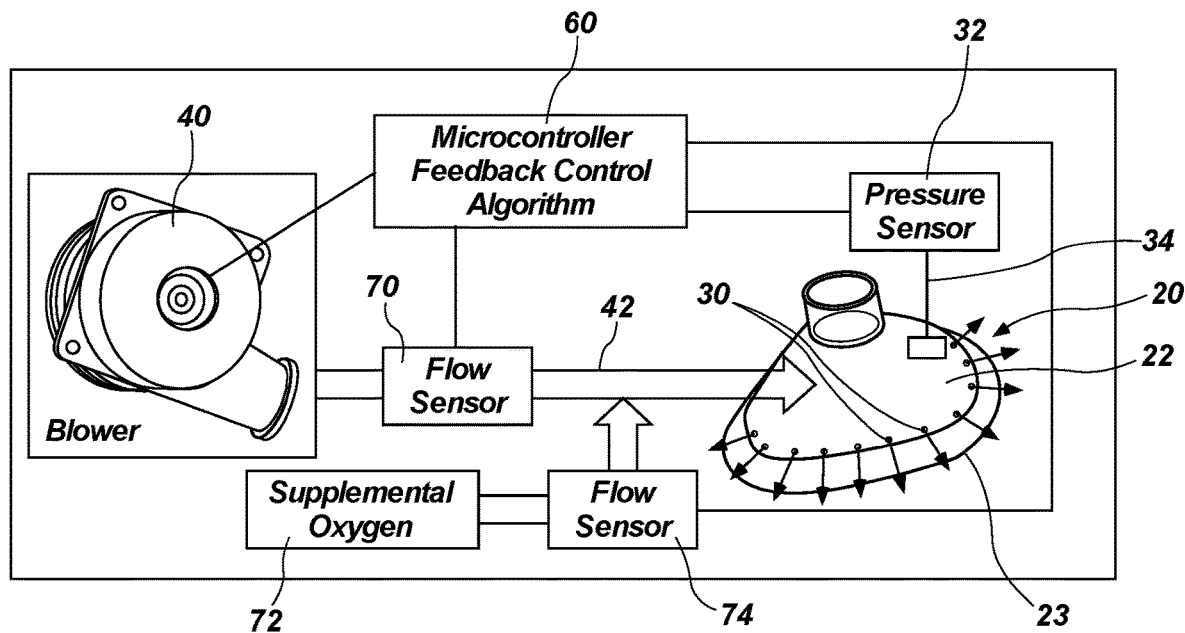
FIG. 3 is a schematic diagram of an exemplary embodiment of a ventilation system as disclosed herein.
Figure 12:
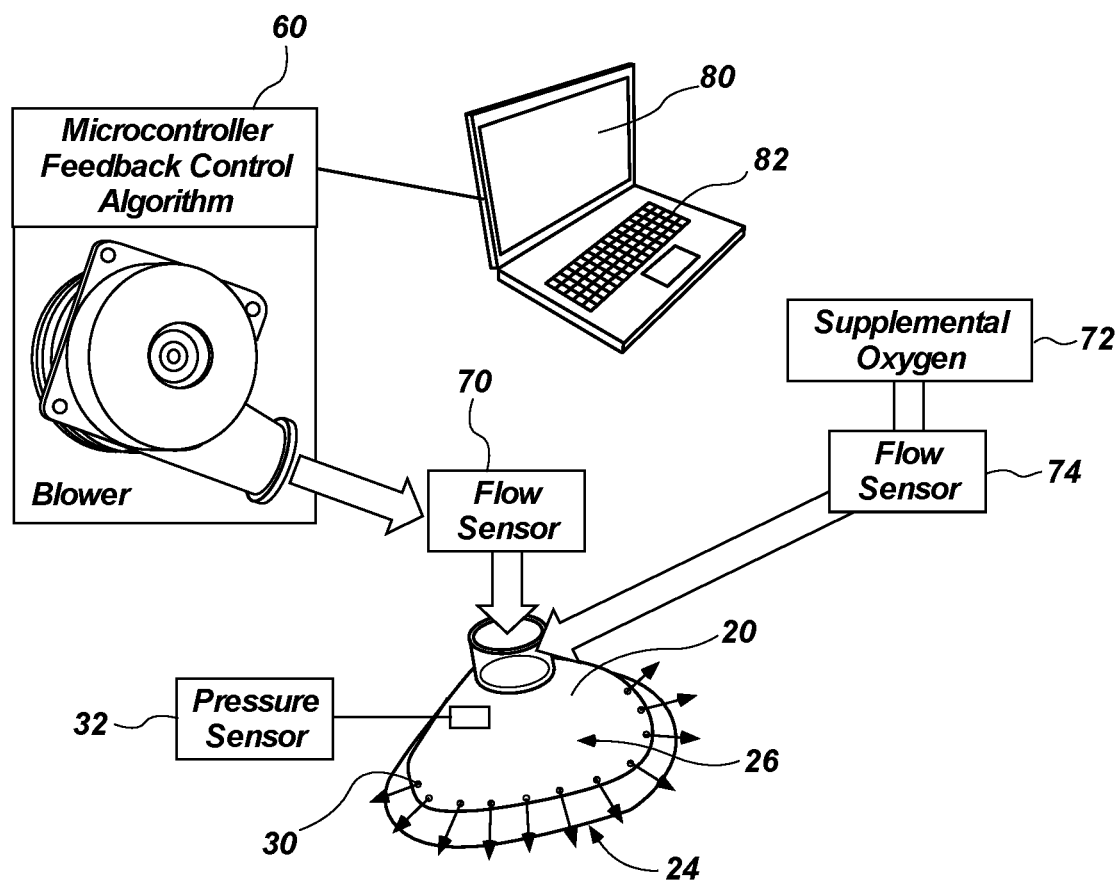
FIG. 12 is a schematic diagram of another exemplary embodiment of a ventilation system as disclosed herein.
Figure 13:
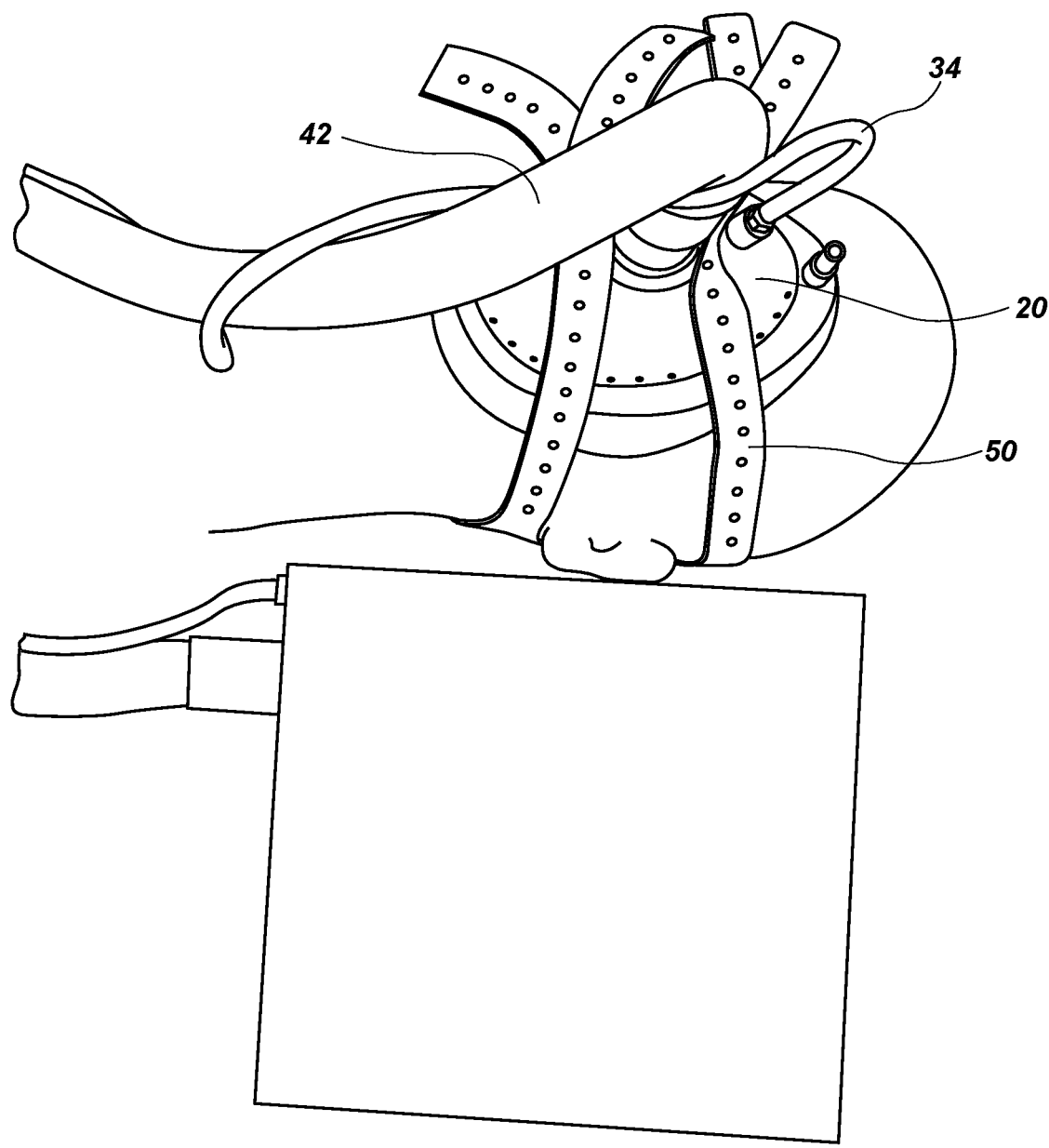
FIG. 13 is an image of another exemplary embodiment of a ventilation system as disclosed herein.

In exemplary aspects, the ventilation system 10 can further comprise a first flow sensor 70 that is positioned in communication with the processor 60 and configured to measure an air flow rate at which air is provided from the blowing assembly 40 to the inlet opening 28 of the mask body 22. Optionally, in these aspects, the processor 60 can be configured to generate an airflow alarm in response to the measured air flow rate falling below a predetermined value. In exemplary aspects, and as shown in FIGS. 3 and 12, the first flow sensor 70 can be positioned in fluid communication with the tube 42 extending between the blowing assembly 40 and the mask 20.

Optionally, in other exemplary aspects, the ventilation system 10 can further comprise an oxygen source 72 positioned in fluid communication with the inlet opening 28 of the mask body 22 and configured to supply oxygen to the mask 20. In these aspects, the oxygen source 72 can be positioned in operative communication with (e.g., be communicatively coupled to, by either wireless or wired connection) the processor 60, and the processor can be configured to control the operation of the oxygen source based upon one or more measured conditions as further disclosed herein. In one aspect, the ventilation system 10 can further comprise a second flow sensor 74 that is positioned in operative communication with the processor 60 and configured to measure an oxygen flow rate at which oxygen is provided from the oxygen source 72 to the inlet opening 28 (or other opening where oxygen enters) of the mask body 22 (for example, via a tube or conduit as depicted in the Figures). It is contemplated that the second flow sensor 74 can be positioned in fluid communication with the tube or conduit extending from the oxygen source 72 to the mask 20. In additional aspects, the processor 60 can be configured to determine a fraction of inspired oxygen ($FiO_2$) value based upon the measured air and oxygen flow rates.

In further exemplary aspects, it is contemplated that the processor 60 can be configured to calculate a leak flow rate according to the equation:

$$\text{Leak Flow Rate} = \text{Leak Factor} \times \text{Mask Pressure},$$

wherein
Leak Flow Rate=the flow rate at which air exits the plurality of leak openings 30 of the mask body 22; and
Mask Pressure=the measured pressure within the mask 20.

In still further exemplary aspects, the processor 60 can be configured to determine a patient flow rate according to the equation:

$$\text{Patient Flow Rate} = \text{Total Flow Rate} - \text{Leak Flow Rate},$$

wherein
Patient Flow Rate=the flow rate of gas inhaled by a patient; and
Total Flow Rate=the flow rate of gas supplied to the inlet opening 28 of the mask body 22.

In these aspects, it is contemplated that the processor 60 can be configured to produce a patient alarm in response to the patient flow rate falling below predetermined value.

In additional exemplary aspects, the processor 60 can be configured to determine a respiratory rate of a subject 100 based upon measured changes in the pressure within the mask body 22. In these aspects, it is contemplated that the processor 60 can be configured to determine a tidal volume of each breath of the subject 100 based upon the determined patient flow rate.

In still further exemplary aspects, the processor 60 can be configured to determine a Leak Factor for each respective breath of the subject 100.

In still further exemplary aspects, the processor 60 can be configured to produce an alarm in response to one or more of the following conditions: a tidal volume of the subject 100 falling below a predetermined volume; a respiratory rate of the subject following below a predetermined rate; a change in resistance in the lungs of a subject; an obstruction in the airway of the subject; and an excessive leak flow rate indicative of a disconnected mask 20.

In operation, and as further disclosed herein, the processor 60 can be configured to shift the ventilation system 10 among a monitoring mode in which the blowing assembly does not actively deliver breaths to the subject 100 (by switching between high and low pressures) and a pressure support mode in which the blowing assembly 40 actively delivers breaths to the subject. In both modes, the processor 60 can be configured to monitor and/or maintain one or more conditions of the ventilation system 10 and the subject 100 as further disclosed herein. Optionally, in exemplary aspects, the processor 60 can be configured to automatically shift the ventilation system 10 among the monitoring mode and the pressure support mode in response to changing conditions of the ventilation system or the subject 100.

Optionally, in exemplary aspects, the blowing assembly 40 and the processor 60 can be operatively associated with the mask 20 to form a multi-component, self-contained ventilation system 10. In further optional aspects, it is contemplated that the ventilation system 10 can be portable. In still further optional aspects, it is contemplated that the ventilation system 10 can weigh less than 3 pounds.

In further exemplary aspects, the ventilation system 10 can comprise a display device 80 positioned in operative communication with the processor 60 and configured to display information regarding one or more conditions of the ventilation system 10 or a subject 100. Optionally, in these aspects, the display device 80 can comprise a user interface 82, such as, for example and without limitation, a touch screen display or keyboard as are known in the art. In exemplary aspects, the display device 80 can be a computer. Optionally, in some aspects, the processor 60 and display device 80 of the ventilation system 10 can be provided as a computing device. However, it is contemplated that the processor 60 and the display device 80 can be operatively associated with the other components of a portable ventilation system 10 as further disclosed herein.

In exemplary aspects, the ventilation system 10 does not comprise a source of compressed gas. In fact, it is contemplated that the disclosed ventilation systems and methods do not need a source of compressed gas to function as described herein.

Optionally, in additional exemplary aspects, the mask 20 can comprise a chin support assembly 50, such as one or more straps, coupled to the mask body 22. In these aspects, it is contemplated that the chin support assembly 50 can be configured to maintain a desired posture and/or orientation of the head of a subject 100 during use of the ventilation system 10.

Figure 4:
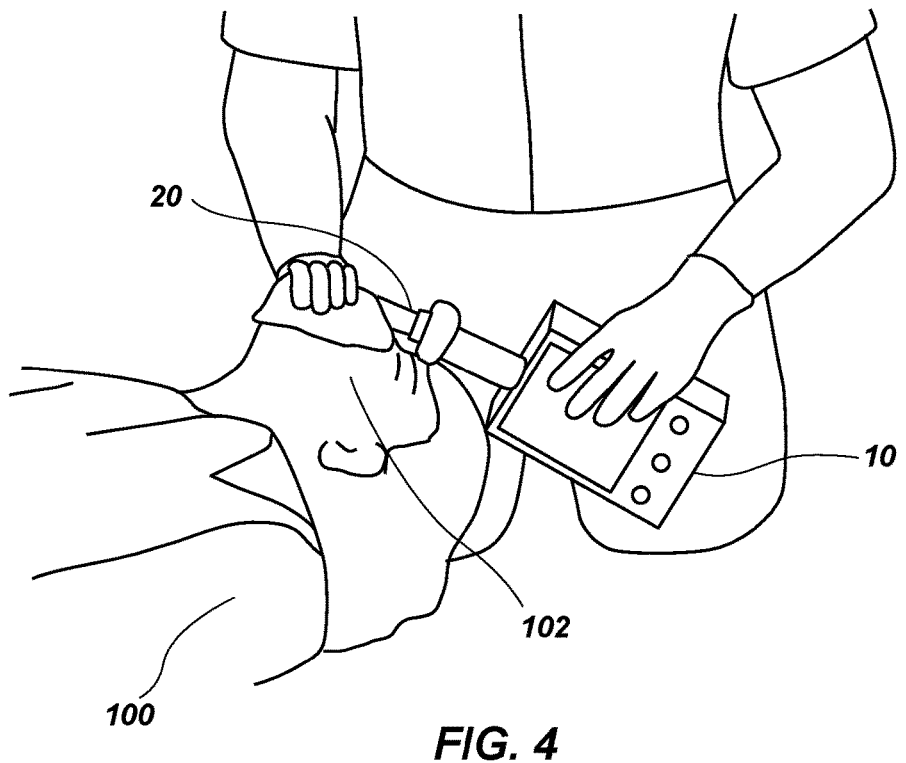
FIG. 4 is a drawing showing an exemplary embodiment of the ventilation system in use as disclosed herein.

In further exemplary aspects, and as shown in FIG. 4, it is contemplated that the ventilation system 10 can be configured for one-handed operation by a user. Optionally, in these aspects, the ventilation system 10 can comprise a button or other input element that can be selectively engaged by a user to initiate delivery of ventilation support to a subject 100. When a chin support assembly 50 is used as disclosed herein, it is contemplated that the chin support assembly can lift the chin of the subject 100 to permit operation of the ventilation system 10 using one hand.

In still further exemplary aspects, the ventilation system 10 can comprise a power source. Optionally, in these aspects, the power source can be a rechargeable battery. In exemplary aspects, the power source can be a rechargeable battery that can provide power to the ventilation system 10 for at least eight hours on a single charge.

Figure 7:
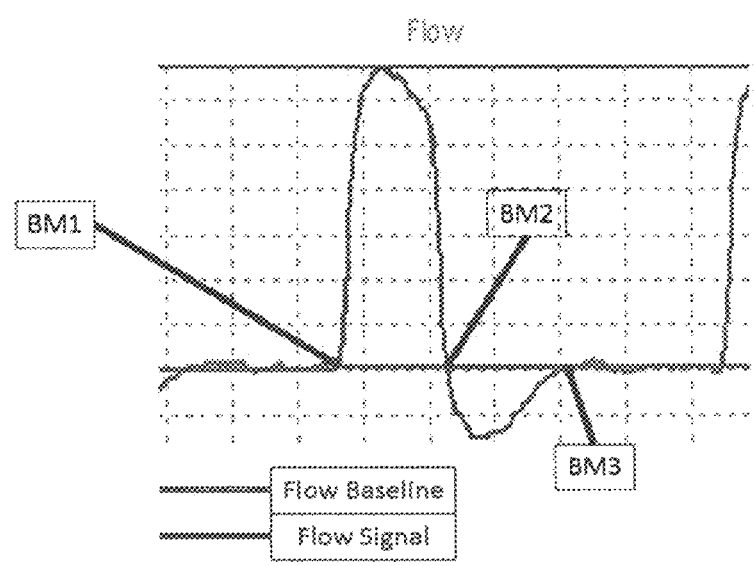
FIG. 7 is a graph depicting a measured flow signal with breath marks (BM1, BM2, BM3) indicated.

In operation, and with reference to FIG. 7, the processor 60 can be configured to monitor and determine the respiratory rate of the subject 100. For example, the processor 60 can be configured to determine a first breath mark (BM1) that corresponds to the start of inspiration and a new breath. The first breath mark can correspond to a point when the flow signal passes above a flow baseline plus a threshold value that can be adjusted according to desired settings. The processor 60 can be configured to then determine a second breath mark (BM2) that corresponds to the end of inspiration and the start of expiration. The second breath mark can correspond to a point when the flow signal passes through the flow baseline. The processor 60 can be configured to then determine a third breath mark (BM3) that corresponds to the end of the breath. This third breath mark can correspond to a point when the flow signal passes through the flow baseline less the threshold value.

As further disclosed herein, the processor 60 can be in communication with a memory that stores software for characterizing the leak of air from the mask 20 as a function of mask pressure. In between breaths during CPAP, all of the flow from the blowing assembly is escaping through the leak of the mask 20. Between BM3 and BM1, the flow signal can be averaged to determine a new flow baseline. During this period, the Leak Factor can be determined, and the leak flow can be calculated as a function of mask pressure as disclosed herein. Thus, when the pressure within the mask 20 increases, the leak flow also increases. As further disclosed herein, a new leak factor can be calculated each breath to allow the ventilation system 10 to adapt to changing mask leak conditions.

In exemplary aspects, the processor 60 can be provided as part of a computer, a remote handheld device, a tablet, a smartphone, a microcontroller, and the like. In these aspects, it is contemplated that the processor 60 can be communicatively coupled (e.g., through a wired or wireless connection) to a memory and/or a remote or Cloud-based network that provides the processor with access to stored protocols, patient data, and other information necessary to perform the methods disclosed herein. Thus, it is contemplated that the processor 60 can be configured to run programs that are stored on a memory or network that is in communication with the processor. Such communication can be through any conventional means, including both wireless and wired connections. In exemplary aspects, the processor 60 can comprise a plurality of processing units or modules that are configured to perform various functions, such as, for example and without limitation, processing of the signals received from the pressure sensor, activation of the blowing assembly, and the like. Although disclosed herein as a single processor 60, it is contemplated that the disclosed system can include more than one processor that cooperate to perform the functions of the processor 60 disclosed herein. For example, in one exemplary aspect, and as shown in FIG. 12, it is contemplated that the ventilation system can comprise a microcontroller that is communicatively coupled to a separate computing device, such as a computer. In further exemplary aspects, as described herein, it is contemplated that the processor 60 can be positioned in communication with the user interface 82, such as a keyboard, a touchscreen display, a computer mouse, a joystick, a remote control, a handheld device, a tablet, and the like, that is configured to receive inputs from a user related to the pacing or recording of electrical activity within cardiac tissue as further disclosed herein. For example, in exemplary aspects, it is contemplated that the user interface 82 can comprise knobs that can be selectively positioned to modify selected pacing wave parameters.

Thus, in use, the processor 60 can use breath marks to make the various calculations used in the alarms and patient monitoring included in the system. By calculating a new leak factor for each breath, the processor 60 can adapt to changing leak conditions. It is contemplated that the thresholds for breath detection and other events can be modified as part of the firmware of the system or as a user designated setting.

EXAMPLES

Example One

Disclosed herein are ventilation devices and systems for improving respiratory monitoring and support. In one aspect, disclosed are algorithms and hardware that can lead to a ventilation device 10, as disclosed herein, for reducing, detecting, and treating respiratory complications in sedated, spontaneously breathing patients, preventing life threatening situations and even death. The disclosed ventilation device 10 is robust, simple to use, and can lower medical costs and improve results.

Respiratory complications, including apneic events, occur in 6% of patients who have been sedated to facilitate procedures such as colonoscopies, often from obstructed airways. These respiratory complications can and do lead to serious and life-threatening situations. Similarly, if a patient in the operating room is anesthetized to be intubated, but the intubation is difficult, the patient requires immediate respiratory support until a more intensive intubation attempt can be made, to prevent severe morbidity. The typical approach in these cases is to temporarily ventilate the affected patient by hand, using a face mask and a bag that is periodically squeezed to deliver breaths. This requires skill, both hands, and completely involves one clinician who is not able to assist elsewhere. Intensive Care Unit ventilators are an option in hospital settings, but they are bulky, expensive, and complicated, requiring specially trained personnel.

The disclosed ventilation devices and systems can provide continuous positive airway pressure, which can help prevent the airway from obstructing due to soft tissue collapse. In one aspect, the ventilation device 10 can monitor tidal volume, respiratory rate, and airway resistance. If a respiratory complication is detected, the ventilation device 10 can increase respiratory support to provide a breath to the patient and warn the clinician. In effect, the ventilation device can reduce respiratory complications and replace the need for manually bag-ventilating the patient. In another aspect, the tested algorithms can create reliable and continual respiratory support and monitoring even in the presence of large or varying leaks around the patient's face mask. Using a digitally controlled miniature radial blower and a strategy to minimize power consumption, the ventilation device 10 can be small (about 8×6×2 inches), can operate without compressed gas, and can run on batteries for up to 8 hours at a time, if needed.

It is contemplated that the ventilation device 10 can be small and easy-to-use. It is further contemplated that the ventilation device 10 can reduce, detect, and treat respiratory complications in sedated, spontaneously breathing patients, thereby preventing unnecessary patient morbidity.

The American Society of Anesthesiology Task Force on Sedation and Analgesia found drug-induced respiratory depression and airway obstruction to be the primary cause of morbidity associated with sedation and analgesia. When a person is incapable of adequate spontaneous breathing, mechanical ventilation is commonly used. Such situations include patients during emergency situations and transport, sedated patients or anesthetized patients between intubation attempts in clinics and hospitals and at other critical times. In most cases, when respiratory support is indicated but intubation is not possible or not deemed necessary, clinicians use a self-inflating manual ventilator or bag-valve-mask (BVM). It is often the only form of life support for an unconscious patient before being intubated and placed on a ventilator. This manual ventilation is a difficult technique to master and requires the full attention of the person performing the ventilation, creating the need for additional staff to assist in vital patient care. Further, there is no indicator that lets the clinician know whether the respiratory rate or tidal volume are adequate, which can lead to considerable patient risk and even death.

This is sometimes mitigated with continuous positive airway pressure (CPAP) through a patient mask. CPAP is a form of non-invasive ventilation (NIV) support. It may be used to hold the airway open during procedural sedation, following sedation, and during monitored anesthesia care (MAC) when patients are sedated but are not intubated. Existing low cost disposable CPAP devices use high flow oxygen to generate CPAP. They do not work well when the mask leak is changing nor do they provide monitoring of airway pressure or tidal volume. The ventilation device, as disclosed herein, can be a portable (1.4 kg) mask ventilation system 10 that can provide ventilation and CPAP with fully integrated reliable ventilation monitoring and alarms. It is contemplated that the ventilation device can effectively combine the portability and ease of use of the BVM with the high-tech monitoring and patient support of NIV.

In one aspect, the ventilation device 10 can compensate for mask leaks and can deliver CPAP to hold the airway open during obstructive apnea. In another aspect, the ventilation device 10 can deliver mandatory pressure support breaths to ventilate during periods of apnea that occur between intubation attempts or during procedural sedation, for example. The ventilation system 10 can have an integrated flow sensor and algorithms that measure patient tidal volume even while compensating for changing mask leak. The ventilation system 10 can use a change in mask pressure to force gas into the lungs and deliver the tidal volume. It is contemplated that the ventilation device 10 can inform the clinician of whether the exhaled breath volume, in response to the pressure change, is sufficient to maintain adequate ventilation. It is further contemplated that the ventilation system 10 can measure the flow of supplemental oxygen and can calculate the resulting inspired oxygen fraction ($FiO_2$) delivered to the patient.

During manual ventilation using a BVM, the clinician's full attention is needed to hold the mask in place and to give breaths. One hand is needed to hold the mask tightly to the patients face with the thumb and index finger to prevent leaks while also holding the airway open with the smaller digits to allow breathing during airway collapse. The other hand is used to carefully squeeze the bag to ensure adequate tidal volume while being careful not to over-pressure the lungs and cause harm. Because this task requires the full attention of the person giving ventilation, a second clinician is needed to perform additional patient care tasks such as administering medications and providing other care. The ventilation device 10, as disclosed herein, can allow clinicians the option of securing the ventilation device with a single hand. It is contemplated that the ventilation device 10 can be held in place using a simple disposable elastomeric strap (H-strap).

The ventilation device 10 can be used in a variety of situations including patient monitoring and support during procedural sedation (for example and without limitation, in a colonoscopy). Millions of procedural sedations are performed each year in the U.S., with many performed during colonoscopies. Sedation agents cause respiratory depression, a combination of apneic events and/or oxygen desaturation. It is known to one skilled in the art that respiratory depression is observed in up to 6% of procedures with sedation. Due to the nature of these procedures and the lack of patient monitoring, this number is likely underestimating the occurrence of respiratory depression during procedural sedation.

It is contemplated that the ventilation device 10 of the present disclosure can reduce the incidence of apneic events in a clinical setting on spontaneously breathing patients undergoing anesthesia or sedation.

The addition of CPAP can pneumatically splint the airway open for the patient during sedation and allow them to breathe spontaneously. It is contemplated that the ventilation device 10 disclosed herein can reduce the number of apneic events as compared to the current standard of care.

Additionally, it is further contemplated that the ventilation device 10 can reduce the risk of barotrauma, hypoventilation, and hyperventilation. In one aspect, as described herein, the ventilation device 10 is a portable positive pressure ventilation device that can provide leak adaptable ventilation monitoring and can have an automatically selected level of ventilation assistance. In another aspect, the ventilation device 10 can reduce operator error, comply with guidelines for ventilation, and improve a clinician's ability to perform other critical tasks.

Respiratory Depression

Most agents used to induce and maintain general anesthesia also drastically affect the drive of the patient to breathe. Breathing is controlled both behaviorally as well as chemically and anesthesia negatively alters both. Anesthesia can also cause respiratory depression by sedative-induced airway collapse. This is where the muscles surrounding the airway are relaxed to the point that they can no longer support the tissue surrounding the airway. There is not an accepted standard definition of respiratory depression, but it is commonly described as a combination of apneic events and/or oxygen saturation. The most common metric defining respiratory depression is a breath rate below 8-10 breaths/minute and/or oxygen desaturation of less than 80%-90% $SpO_2$. Much of the research that has been aimed at apnea focuses on sleep apnea, but the principles translate well to opioid induced respiratory depression. Respiratory depression, if not properly addressed, is a serious and life threatening problem.

Respiratory depression is also common during procedural sedation where sedatives and analgesics are administered to facilitate a procedure without inducing general anesthesia. Millions of procedural sedations are performed each year in the U.S., for example during colonoscopies. Sedation agents cause respiratory depression, a combination of apneic events and/or oxygen desaturation. It is known in the art that there are clinically significant respiratory complications in up to 6% of procedures with sedation. In the study disclosed herein, 26 sedated patients undergoing a colonoscopy with an average of 2.69 apneic events per patient were observed. The disclosed ventilation device 10 can address this problem by providing respiratory support and monitoring during procedural sedation. It is contemplated that the ventilation device 10 can also be extended to a variety of other applications and situations, in which respiratory depression is an issue.

Figure 1:
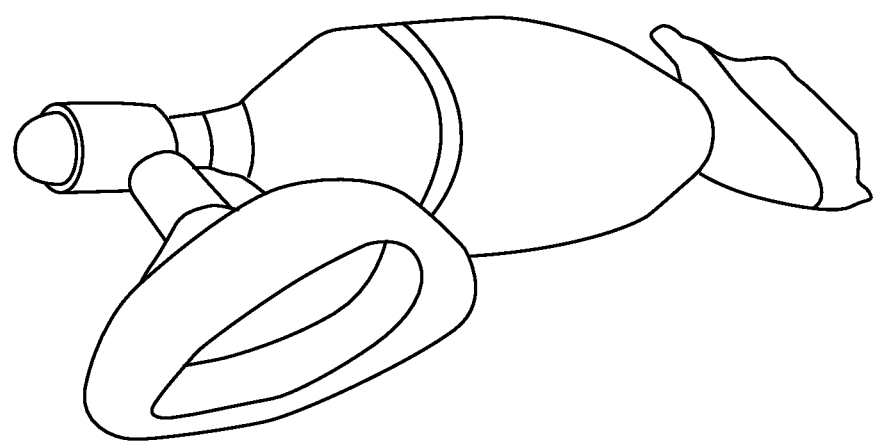
FIG. 1 is an image showing a traditional bag-valve mask used to deliver manual ventilation, as is known in the art.

In one aspect, the ventilation device 10 can provide the portability of BVM and the sophisticated ventilation support and monitoring of high-end and expensive NIV. The ventilation device 10 described herein can combine the benefits of BVM and NIV devices while avoiding their shortcomings:

Bag-Valve Mask Ventilation. A typical BVM, as shown in FIG. 1, is used to perform emergency manual ventilation during transport, between intubation attempts, and at other critical times when the patient is incapable of adequate spontaneous ventilation. The bag valve mask consists of a flexible air chamber attached to a facemask via a shutter valve. When the bag is compressed, it forces air through the valve and into the patient's airway. When it is released, the bag refills with air and the shutter valve closes until the next compression.

Figure 2:
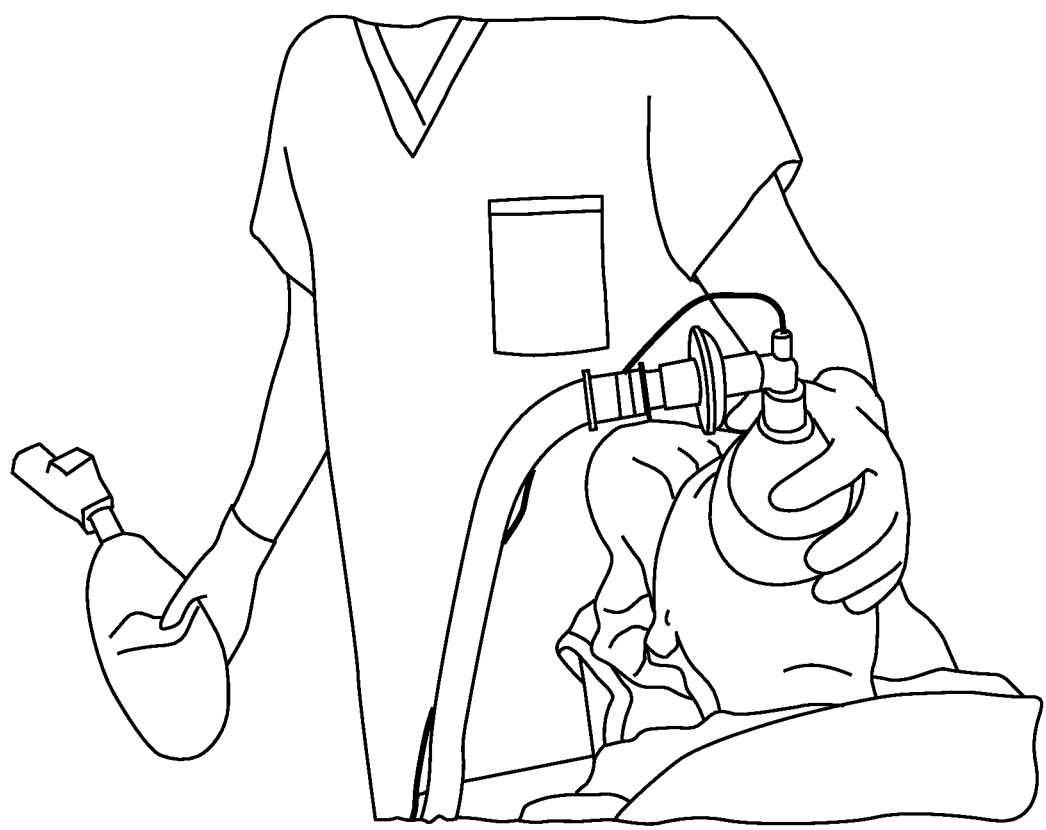
FIG. 2 is an image showing manual ventilation using a bag-valve-mask (BVM) built into an anesthesia machine, as is known in the art.

The bag valve method is a difficult technique to master and requires the full attention and both hands of the person performing the ventilation. In the operating room, as shown in FIG. 2, manual ventilation can be performed by squeezing the anesthesia bag while holding the mask to the patient in a similar manner as when using a BVM. Many novice clinicians have difficulty maintaining an open airway while giving breaths. One hand is needed to grasp the mask tightly to the patients face to prevent leak while using two fingers to provide the required chin-lift and the proper head-tilt to keep the airway open. The other hand is used to carefully squeeze the bag to ensure adequate tidal volume while being careful not to over-pressure the lungs and cause barotrauma. If the airway is obstructed, the clinician, who is squeezing the bag, may mistakenly think there is an adequate tidal volume being delivered when in fact, the entire tidal volume may be lost through a leak between the mask and the patient's face. Because this task requires the full attention of the person giving ventilation, a second clinician is needed to perform additional patient care tasks, such as administering medications and providing other care.

It is difficult for the person operating the BVM to adequately ensure that the patient they are ventilating is receiving the correct respiratory rate. Clinical studies reveal that trained clinicians give on average 25-35 breaths per minute (bpm), not the 10-12 bpm prescribed by guidelines. Keeping artificial breath rates low is difficult because the high adrenaline state of the operating room alters time perception and the rapidly refilling bag sets up a reflex in which the clinician is inclined to deliver breaths as soon as the bag inflates. Successful BVM is classified as approximately 8-10 mL/kg fresh gas flow and an upper limit pressure of 20-25 cm $H_2O$.

It is also difficult for the person operating the BVM to adequately ensure that the person they are ventilating is receiving the correct tidal volume. Excessive pressures from tidal volumes that are too high can cause a decrease in cardiac preload, traumatic brain injury, hemorrhagic shock, gastric insufflation, and lung injury. Inadequate pressure can lead to the patient not receiving adequate oxygen delivery and carbon dioxide removal.

Difficult or impossible mask ventilation is defined as inadequate gas flow, unstable ventilation, or requiring of an additional provider. The incidence rate of difficult or impossible mask ventilation is reported as 1.4%. The factors that contribute to difficult mask ventilation are mostly physiological and patient specific. There are multiple references calling for additional BVM training to medical staff in order to raise consistency and avoid complications.

Airway Support

When a patient is overweight, there is extra soft tissue surrounding the airway that may cause it to collapse and obstruct when the patient is under sedation. In the U.S., 30% of adults 20 years and older are obese. Furthermore, it is estimated that there are 300 million obese people worldwide and another 750 million people who are overweight. In many sedated patients, the patient's spontaneous respiration is adequate if the airway is supported so that inspiratory flow is unobstructed by soft tissue around the airway. The clinician can support the airway manually using a chin lift, jaw thrust, or by inserting an artificial airway if sedation is sufficiently deep. An alternative method of supporting the airway is using CPAP, which uses elevated air pressure inside the airway to hold the airway open against sagging soft tissues so that the patient can breathe. In CPAP, a mask is placed on the face and air flows constantly into the mask out of a leak port in the mask so that the airway is slightly pressurized at all times. Obstructive Sleep Apnea patients are often prescribed home-use CPAP machines in order to prevent their soft tissues obstructing their airways during sleep, CPAP can be given using simple constant flow generators such as the Boussignac device or using feedback controlled systems that maintain set airway pressure regardless of mask tightness and leak. These feedback controlled systems are generally large, expensive, and complex (e.g., V60 noninvasive ventilator, Philips-Respironics, Carlsbad, Calif.). The ventilation device and system of the present disclosure can provide the benefits of the larger system in a small (approximately 8×6") battery operated package.

Non-Invasive Ventilation.

Non-invasive ventilation (NIV) is a technique that is growing rapidly in popularity for mask ventilation support, primarily in intensive care units (ICU). CPAP is one example of NIV. NIV avoids placing any devices inside of the patient's airway but instead supports a compromised airway with a pneumatic splint of air pressure. Compared with endotracheal intubation, NIV reduces the length of ICU and hospital stay, morbidity, and mortality in patients with acute and chronic respiratory failure. Current noninvasive ventilators are physically large and expensive. To facilitate patient monitoring and accurate breath triggering, they require a precise fitting of the mask to each patient using a complex headgear that cannot be stretched. This tight seal to the patient's face allows the machine to accurately calculate the tidal volume delivered to the patient since the leak conditions are stable and can be well characterized. While these large devices would function during an emergency situation, they are too large to accommodate a patient in transport and too expensive to have readily available in every setting where sedation ventilation is needed. A typical noninvasive ventilator includes features such as complex breath triggering and high levels of pressure support capability that are needed to treat ICU patients suffering from respiratory disease, but are not needed for sedation ventilation or simple airway support.

The ventilation device and system, as disclosed herein, can be a noninvasive ventilator which can be optimized to meet the needs of sedation respiratory support and airway support. It is contemplated that the breath delivery, monitoring algorithms, flow generator, and sensors can be modified and simplified to meet the conditions that are unique to sedation respiratory support. It is contemplated that the ventilation system can provide the following aspects:

Pressure Control: Ability to deliver pressure support ventilation up to 25 cm $H_2O$ (1250 ml tidal volume in a typical patient) without the need for compressed gas from the wall or tanks with automatic mask leak compensation;

Integrated Monitoring: Integrated monitoring of the patients breathing and inspired oxygen. Tidal volume calculation and breath rate measurement even when using a poorly fitted mask that is held in place with variable force (hand or disposable elastomeric strap) during the breath;

Leak Compensated, Monitored CPAP: Leak compensated continuous positive airway pressure (CPAP) up to 25 cm $H_2O$ to support a collapsed airway; and Portability: Long battery life (>8 hours on a single charge) in a package weighing less than 3 lbs.

Pressure Control

The ventilation system 10 of the present disclosure can use a high performance miniature radial blower (for example and without limitation, a model U51DL-4 from Micronel US, LLC), as shown in FIG. 3, to generate precise flows and pressures under microprocessor control. A pressure sensor 32 (for example and without limitation, a BLVR-L01D sensor, AllSensors, Morgan Hill, Calif.) can measure mask pressure and the system software can control the speed of the blower 40 to provide precise mask pressure regardless of mask leak. The ventilation system 10 can ventilate the patient by periodically raising the mask pressure so that gas can be forced into the patient's lungs. The volume of each breath can be determined by the amount of pressure support, and the patient's lung (and chest wall) compliance. In a typical patient with compliance of 50 ml/cm $H_2O$, pressure support of 10 cm $H_2O$ will result in a 500 ml breath. The disclosed ventilation system 10 can deliver pressure support breaths of up to 25 cm $H_2O$.

Major hazards of manual mask ventilation include barotrauma (pressure damage of the lungs) and esophageal ventilation where gas is forced into the stomach rather than the lungs. The mask pressure of the present ventilation system 10 can be precisely controlled so that it does not exceed the opening pressure of the esophageal sphincter (20-25 cm $H_2O$) to avoid forcing gas into the stomach rather than into the lungs.

As shown in FIG. 4, the ventilation system 10 can be used in Auto-Mode to deliver ventilation to an unconscious patent. In exemplary non-limiting aspects, a clinician using this mode can expect the following:
  CPAP to maintain open airway
    Easy one-finger chin-lift
  BiPAP breath delivery—bi-level positive airway pressure
  Easily adjusted pressure levels
  Instant tidal volume measurement
  Set respiration rate as high as 20 breaths/min
  Clinician can manually trigger breaths with physical switch Integrated Monitoring The ventilation system 10 can incorporate a differential pressure type flow sensor (for example and without limitation, a MPXV5004DP sensor, FreeScale Semiconductor, Austin Tex.) that can continuously measures the flow from the blower and supplemental oxygen going to the patient. Using the known flow and mask pressure signals, the software can characterize the amount of leak at each pressure level for each breath. After the leak flow has been compensated for, the system can calculate the flow of gas into and out of the patient for each breath. Continuous monitoring of the delivered breath can give the user information about effective ventilation and can provide alarms for airway obstruction and other causes of inadequate ventilation. The ventilation system 10 can also monitor mask pressure and alarms if the leak is so large that a minimum mask pressure cannot be maintained. The monitoring algorithms typically found in a noninvasive ventilator have been modified so that measurements can be made even when the position of the mask relative to the face is not constant. For instance, when the mask is held in place by hand or using an elastomeric H-strap that is typically used in anesthesia and emergency care, the mask can move slightly off the face when mask pressure is raised. Non-invasive ventilators designed for ICU use cannot make accurate measurements in this condition and typically give alarm messages when the mask leak is unstable. The mask position requirements of the algorithm can be relaxed, making it more robust and reliable. In addition, the ventilation system 10 can measure the flow of supplemental oxygen that is added into the breathing circuit and, combined with the blower flow signal, calculate the inspired oxygen fraction ($FiO_2$) that is being delivered to the patient on each breath. The clinician is then able to adjust the flow of oxygen according to the needs of the patient.

Leak Compensated, Monitored CPAP

Figure 5:
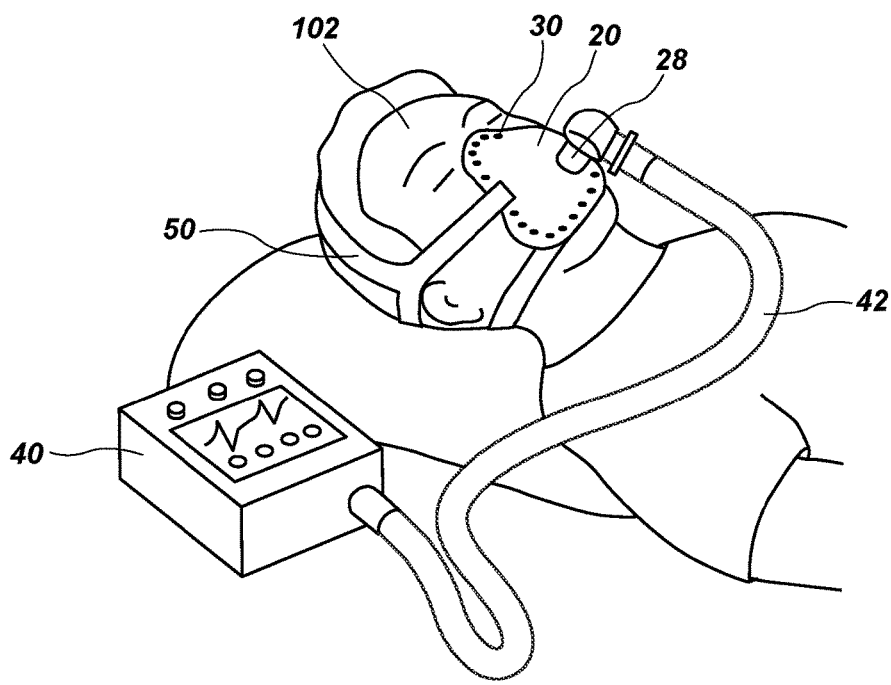
FIG. 5 is a drawing showing an exemplary embodiment of the ventilation system in use as disclosed herein.
Figure 6:
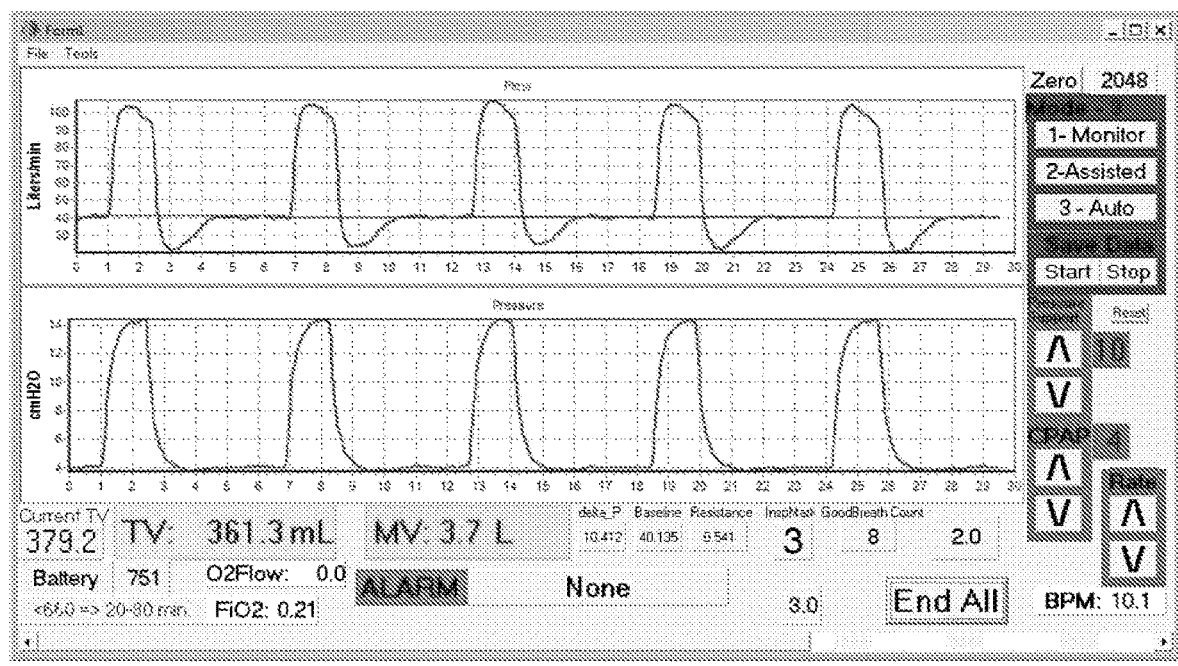
FIG. 6 is screenshot of an exemplary user interface for an experimental prototype ventilation system as disclosed herein.

The ventilation device 10 can utilize CPAP to support the airway of a sedated patient who is at risk for airway collapse. By holding the mask pressure at a fixed constant level under feedback control, the ventilation system 10 can maintain airway support. The ventilation system 10 can automatically leak compensating so that the mask 20 can either be held in place manually by the clinician or can be secured using a common disposable elastomeric H-strap (shown in FIG. 5). Because the ventilation system 10 can monitor respiratory rate and tidal volume during CPAP, the clinician can be aware of slowed respiratory rate caused by opioid medication and/or of upper airway obstruction. The present ventilation system 10 can provide high level of possible CPAP (up to 20 cm H2O) and full patient monitoring and alarms while in CPAP mode. As shown in FIG. 5, the ventilation system 10 can be used in Monitor-Mode to deliver ventilation to a breathing patient. In exemplary non-limiting aspects, a clinician using this mode can use the system to perform the following tasks: set level of CPAP; monitor the patient's breathing (e.g., Respiration rate, Tidal volume, $FiO_2$); use the "smart monitor mode" to automatically trigger breaths if no breathing is detected from the patient and automatically raise the level of CPAP if no breaths are detected. In use, it is contemplated that the mask 20 of the ventilation system 10 can be held in place by a conventional elastomeric H-strap.

Portability

In order to adequately replace the BVM devices for use during transport, the ventilation device 10, as disclosed herein, can be portable. For instance, it is contemplated that the ventilation device 10 can be portable and lightweight at approx. 1.4 kg and can occupy a volume similar to a BVM (about 1.5 L or 96 in$^3$). It is further contemplated that the ventilation device 10 can be powered by a rechargeable battery that provides ventilation and monitoring for an excess of 8 hours. The battery can power the electric blower to be able to deliver pressures up to 25 cm $H_2O$, which is above what is necessary physiologically.

The combination of pressure 32 and flow sensors 70, 74 of the present ventilation device 10 can automatically detect when the mask 20 is placed on the face of the patient to ventilation support. Likewise, when the mask 20 is not in use, the blower 40 can automatically shut down to conserve battery power and reduce noise.

Comparison with Other Devices

The ventilation device 10 described herein can provide many benefits over existing devices. The disclosed ventilation device 10 can replace the bag-valve mask devices that are commonly used as well as bring the benefits of expensive NIV devices to more wide reaching applications. One competing device on the market is the SAVeII™ by AutoMedx Inc. Table 1 outlines the advantages the present ventilation device over a BVM as well as the SAVeII™.

TABLE 1

Comparison of the disclosed ventilation device to SAVe II ™ and BVM.

| Feature | Ventilation Device | Bag Valve Mask | SAVe II ™ |
|---|---|---|---|
| Leak Compensation | Full compensation for leaks up to 40 L/min | None | None |
| Airway Support | Automatic with integrated CPAP capability | Manual with user hands | Manual with user hands |
| Ventilation Modes | Monitor Mode (CPAP only) Auto Mode (BiPAP) Pressure controlled, volume monitored | Manual | Auto Mode (BiPAP) Volume-targeted Pressure limited |
| Settings | | | |
| TV (mL/breath) | 50-1000 (any increment) | Varies with bag size | 200-800 (increments of 50) |
| Respiration Rate | 4-25 | Unlimited | 8-20 |
| Inspiratory Flow | Up to 50 L/min | None | Up to 27 L/min |
| PIP Limit (cmH$_2$O) | 0-40 | Varies | 10-60 |
| PEEP (cmH$_2$O) | 0-20 cm H2O | None | Internal: 0-10 H2O, intubated only |
| Alarms/Indicators | Circuit disconnect Over Pressure/blockage Low battery Breath stacking I:E ratio exceeded Airway resistance change No breaths detected -> Auto Low minute volume Excessive leak/disconnected Tidal volume display Minute volume display Respiration rate display FiO2 display | None | Circuit disconnect Over Pressure/blockage Low battery Breath stacking I:E ratio exceeded |
| Weight | 1.4 kg | Varies, <1 kg | 1.4 kg |
| Display/User Interface | Touch screen display LED indicators | None | LED indicators 7 segment displays Increment/decrement buttons |
| Patient Breathing Circuit | Mask w/built in leak | Passive Breathing Valve | Active Breathing Valve |
| Duration per charge | Up to 20 hrs in monitor mode | N/A | 10 hrs @ TV = 600, RR = 10, PEEP = 5 |
| Monitoring | | | |
| Tidal Volume and respiration rate | Integrated TV and RR monitoring with alarms | None | None |

EXPERIMENTS

During testing, the ventilation system 10 was shown to accurately deliver the set tidal volume to within a few mL, and the set breath rate to within a 50th of one breath per minute. This was accomplished in the presence of leaks of up to 75 L/min. The variability of delivered tidal volumes of the ventilation device was much lower than that of standard BVM. The system 10 achieved adequate removal of CO2 from the mask and breathing hose. When the system 10 was merely monitoring spontaneous breathing, the system showed similar accuracies for monitoring tidal volume and breath rates, even with mask leaks of up to 40 L/min. The alarms (battery low, tidal volume low, obstruction, change in airway resistance) worked accurately and promptly. The prototype noise level stayed <75 dB(A) at one meter distance from the ventilator.

During procedural sedation during a colonoscopy, it is contemplated that the ventilation system 10 can reduce incidence of apneic events in a clinical setting on spontaneously breathing patients undergoing anesthesia. It is contemplated that the addition of CPAP during these procedures can pneumatically splint the airway open for the patient during sedation and allow the patient to breathe spontaneously, resulting in less apneic events than the current standard of care.

Materials and Methods

In use, the nurse and technicians can attach all necessary standard sensors and connect them to the patient and monitoring system. In addition to the standard of care monitors, data can be collected from an additional non-invasive respiratory monitor (chest bands) and saved to a portable personal computer using previously developed custom software for later analysis. Any supplemental oxygen delivered can be left to the clinician's discretion, and the selected amount of supplemental $O_2$ delivered can be recorded to a data sheet. Pressure 32 and flow sensors 70, 72 included in the ventilation device 10 can be used to monitor the patients' tidal volumes during the procedure. Tidal volume calibration can be performed beforehand using the anesthesia machine in the colonoscopy suite.

The ventilator mask 20 can be placed on the patient's face according to their comfort using an elastomeric H-strap 10. CPAP of 4 cm $H_2O$ can be the starting setting for the ventilation device 10. When a period of apnea lasting longer than 30 seconds is detected, pressure support breaths can be given automatically with 10 cm$H_2O$ pressure support. The average lung compliance of the patient population is 0.05 L/cm $H_2O$, thus yielding approximately 500 mL tidal volumes for all pressure supported breaths. If the patient or clinician has any objection or discomfort with these settings, the settings can be adjusted and noted in the data files. The procedure duration and the amount and type of sedatives delivered can be documented. The Observer's Assessment of Alertness/Sedation (OAA/S) scale can be assessed and recorded at five minutes after each adjustment of sedation medication delivery until procedure completion.

A sample size of 30 patients was calculated to have a 90% power to detect a difference in means of apneic events per patient. Control data was collected in the endoscopy suite on patients undergoing colonoscopies where the ventilation and SpO2 was monitored for patients undergoing procedural sedation. The tidal volume, respiratory rate, CO2, and SpO2 were also monitored for patients undergoing procedural sedation for their colonoscopies. By noninvasively monitoring patients during routine procedures, ventilation patterns were observed that can be used to separate sub-clinical respiratory depression events from critical respiratory depression, which can lead to hypoxia. The control group of 26 patients yielded a mean of 2.69 apnea events per patient (an apnea event was defined as 10 s or longer of zero respiratory flow). The number of apnea events of 10 s or longer can be counted for each patient and compared to the control group. The use of the ventilation device 10 during procedural sedations can eliminate apneas from these procedures and yield an average apnea event per patient of zero.

Evaluation of Monitor Mode

CPAP through a patient mask can be used to hold the airway open during procedural sedation, in the recovery room, and during other monitored anesthesia care when patients are sedated but are not intubated. Low cost disposable CPAP devices use high flow oxygen to generate CPAP but do not compensate well for changing mask leak nor do they provide monitoring pressure level or patient breathing. The disclosed ventilation system 10 (referred to interchangeably as an "EBMV") includes integrated patient monitoring that measures airway pressure, breath rate, and spontaneous tidal volume in the presence of mask leak while maintaining CPAP. We used a bench simulation to evaluate the accuracy of the patient monitoring capability integrated into the prototype system.

Methods: The EBMV was connected to a manikin head via a modified air cushion mask that was held in place using a common elastomeric strap (H-strap). The trachea of the manikin head was connected to one side of a test lung through a gas flow analyzer (VT-Plus, Fluke Biomedical, Everett Wash.) and the other side of the test lung was mechanically ventilated and the two sides of the test lung were mechanically coupled so that spontaneous breathing was simulated in the side connected to the manikin. CPAP was delivered by the test system and respiratory rates and tidal volumes as measured by the CPAP system and the gas flow analyzer were compared. The EBMV measures supplemental oxygen flow and calculates FiO2 from the ratio of flow from its compressor to supplemental oxygen flow. Data was collected over a range of CPAP settings (4, 6, 8 cm H2O), respiratory rates (6, 8, 10, 15, 20 breaths/min), supplemental oxygen flows (1, 2, 3, 4, 5 L/min), and tidal volumes (200 and 500 ml).

Figure 8:
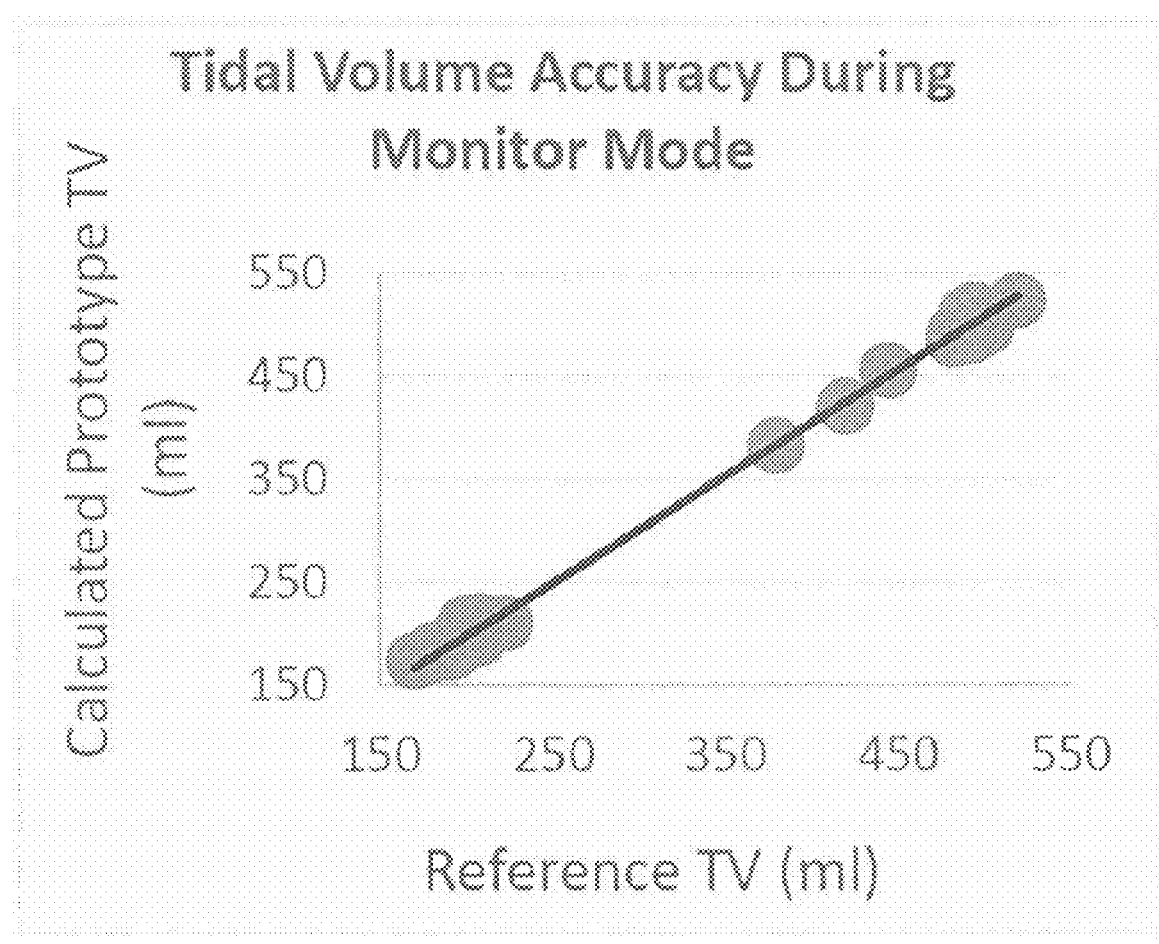
FIG. 8 is a graph of the tidal volume calculated by an experimental ventilation system versus a reference tidal volume measured by a gas flow analyzer during spontaneous ventilation (the monitoring mode of the ventilation system).

Results: The average difference between measured and actual respiration rate was 0.093±0.024 (mean±one standard deviation) breaths per minute. The average difference between FiO2 measured in the test lung and FiO2 calculated by the system was near zero and was too small evaluate using a clinical monitor (CapnoMAC Ultima, Datex, Helsinki Finland). The plot (FIG. 8) shows average error in tidal volume measurement when 200 ml breaths were simulated was 2.93±6.83 ml and was −7.4±7.55 ml when 500 ml breaths were simulated.

Evaluation of Auto Mode

The self-inflating manual ventilator or BVM is used to ventilate patients during transport, between intubation attempts, and at other critical times when the patient is incapable of adequate spontaneous ventilation. The EBMV automatically compensates for mask leak and delivers CPAP to hold the airway open during obstructive apnea and delivers mandatory pressure support breaths to ventilate during opioid induced central apnea. However, if the lungs are stiff (low compliance) the set level of pressure support may not induce large enough tidal volumes for adequate ventilation. The EBMV has an integrated flow sensor and algorithms that measure patient tidal volume even in the presence of mask leak and inform the user of the possible need to use more pressure support. The EBMV also measures the flow of supplemental oxygen and calculates the resulting inspired oxygen fraction (FiO2). We evaluated the accuracy of the integrated tidal volume measurement and FiO2 calculation in the EBMV using a bench simulation. The EBMV measures the total (patient plus leak) flow leaving the ventilator and uses a compensation algorithm to determine the portion of gas that enters the patient.

Methods: The prototype system was connected to a manikin head via an air cushion mask that was modified to include an intentional leak. The mask was held in place using a head strap. The trachea of the manikin head was connected to a test lung through a gas flow analyzer (VT-Plus, Fluke Biomedical, Everett Wash.) that directly measured tidal volume, respiratory rate and airway pressure. These direct measurements were compared against measurements made by the portable ventilator that was connected distal to the patient through the modified mask. Various levels of simulated lung compliance and pressure support were tested. The system was tested over a range of simulated lung compliance (0.10, 0.030, 0.50 L/cm H2O), CPAP (2, 4, 6, 8 cm $H_2O$) and respiratory rate settings (6, 8, 10, 15, 20 breaths/min).

Figure 9:
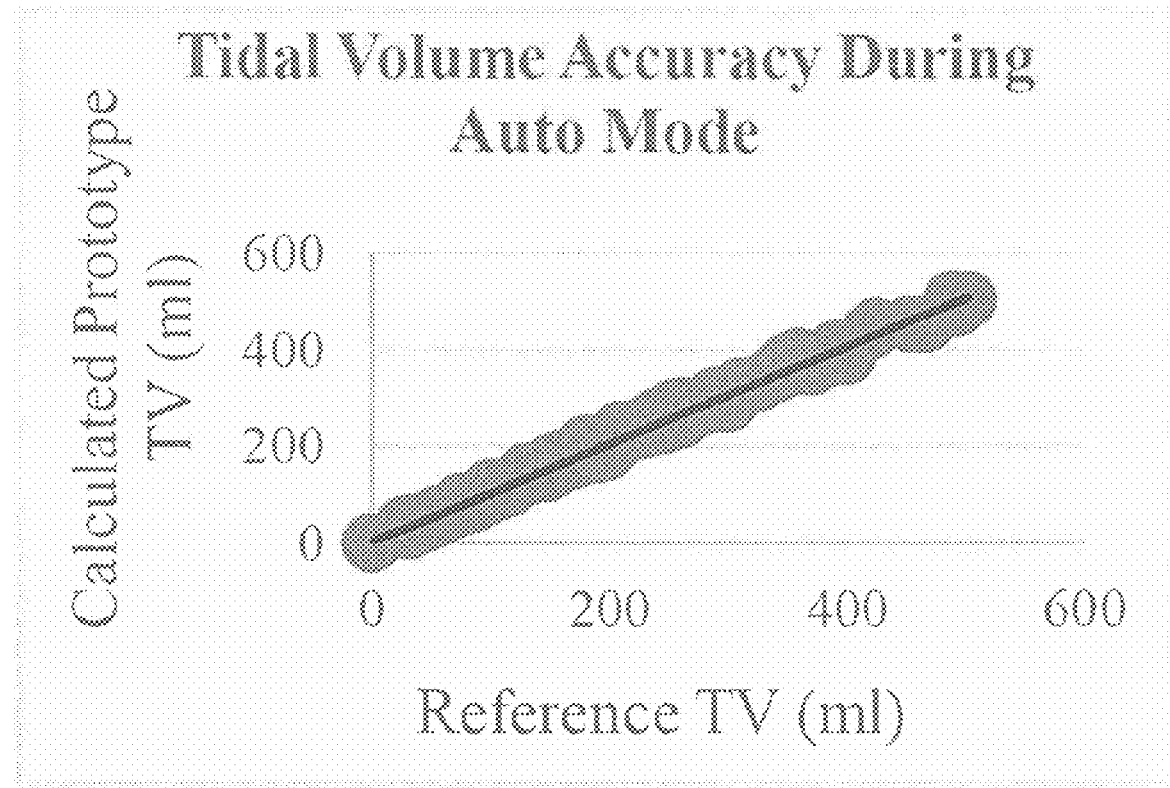
FIG. 9 is a graph of the tidal volume calculated by an experimental ventilation system versus a reference tidal volume measured by a gas flow analyzer during the automatic mode of the ventilation system.
Figure 10:
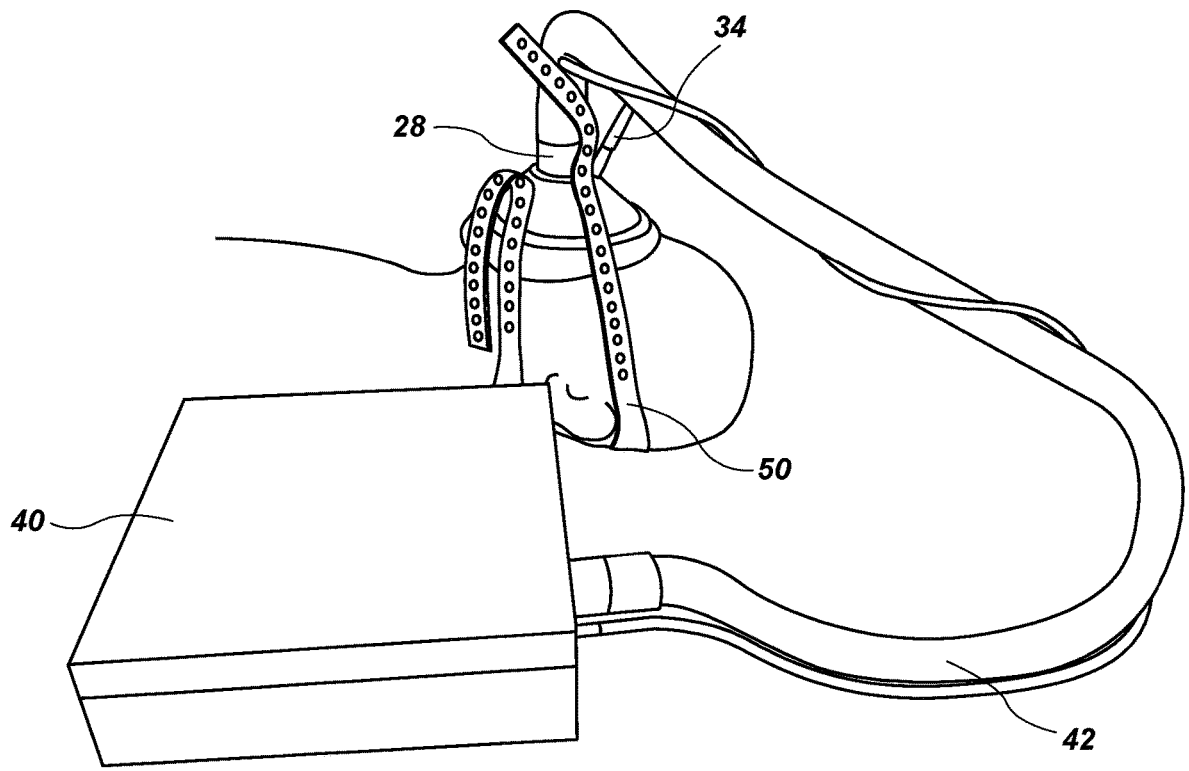
FIG. 10 is an image of an exemplary embodiment of a ventilation system as disclosed herein.

Results: The plot (FIG. 9) shows the tidal volume calculated by the EBMV versus the reference tidal volume as measured by the gas flow analyzer. The average difference in the tidal volume measurement was −4.77±7.02 (mean±one standard deviation) ml. The average difference and standard deviation was consistent over all levels of CPAP that were tested.

Evaluation of Single-Handed Mask Ventilation

During manual emergency patient ventilation using a BVM the clinician's full attention is needed to hold the mask in place and to give breaths. One hand is needed to hold the mask tightly to the patients face to prevent leak while also holding the airway open to allow breathing during airway collapse. The other hand is used to carefully squeeze the bag to ensure adequate tidal volume while being careful not to over-pressure the lungs and cause harm. Because this task requires the full attention of the person giving ventilation, a second clinician is needed to perform additional patient care tasks such as administer medications and provide other care. The EBMV uses pressure controlled high gas flow to compensate for mask leak and generates CPAP to hold the airway open. Mandatory breaths are given by increasing the feedback-controlled mask pressure during inspiration which forces gas into the lungs even where there is mask leak. The mask can be held on the patient manually using a single hand or can be held in place using a simple elastomeric strap (H-strap). We compared the ability of volunteers to deliver breaths in a bench simulation using a conventional BVM and both hands and using the test system with a single hand.

Methods:

The EBMV was connected to a manikin head via an air cushion mask that was modified to include intentional mask leak. The trachea of the manikin head was connected to a test lung through a gas flow analyzer (VT-Plus, Fluke Biomedical, Everett Wash.). The gas flow analyzer directly measured the volumes entering and leaving the test lung. Eight volunteers were asked to deliver 500 ml tidal volumes at six breaths per minute. The same volunteers were then asked to use the prototype system by holding the modified mask on the manikin face using their non-dominant hand while performing a distracting task on their smart-phones with the other hand. The resulting delivered tidal volumes, breathe rates and airway pressures were recorded using the gas flow analyzer. If the mask leak was too high to deliver the full volume, the system alerted the user to apply more pressure to the mask and reduce the leak. The accuracy of the delivered ventilation was measured by the gas flow.

Results:

The average delivered tidal volumes ranged from 207 to 723 ml using manual ventilation and from 420 to 524 ml using the EBMV. The average peak inspiratory pressure ranged from 6 to 16.93 cm $H_2O$ with a single breath maximum of 19.3 cm $H_2O$ using manual mask ventilation and from 13.95 to 14.13 with a single breath max of 14.3 cm $H_2O$ using the prototype system. The prototype system maintained CPAP at 4 cm $H_2O$ throughout the test.

Exemplary Aspects

In view of the described devices, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A ventilation mask comprising: a mask body having an inner surface configured for engagement with a face of a subject and an opposed outer surface; and a pressure sensor operatively associated with the mask body and configured to measure pressure within the ventilation mask, wherein the mask body defines an inlet opening and a plurality of leak openings extending between the inner and outer surfaces of the mask body, and wherein the inlet opening is configured to receive air from a blowing assembly.

Aspect 2: The ventilation mask of aspect 1, further comprising a chin support assembly coupled to the mask body.

Aspect 3: A ventilation system comprising: a mask comprising: a mask body having an inner surface configured for engagement with a face of a subject and an opposed outer surface; and a pressure sensor operatively associated with the mask body and configured to measure pressure within the mask, wherein the mask body defines an inlet opening and a plurality of leak openings extending between the inner and outer surfaces of the mask body; a blowing assembly positioned in fluid communication with the inlet opening of the mask body and configured to direct air to the inlet opening of the mask; and a processor positioned in operative communication with the blowing assembly and the pressure sensor of the mask, wherein the processor is configured to selectively control the blowing assembly based upon at least the measured pressure within the mask.

Aspect 4: The ventilation system of aspect 3, further comprising a first flow sensor that is positioned in communication with the processor and configured to measure an air flow rate at which air is provided from the blowing assembly to the inlet opening of the mask body.

Aspect 5: The ventilation system of aspect 4, wherein the processor is configured to generate an airflow alarm in response to the measured air flow rate falling below a predetermined value.

Aspect 6: The ventilation system of aspect 4, further comprising an oxygen source positioned in fluid communication with the inlet opening of the mask body and configured to supply oxygen to the mask.

Aspect 7: The ventilation system of aspect 6, wherein the oxygen source is positioned in operative communication with the processor, and wherein the processor is configured to control the operation of the oxygen source based upon one or more measured conditions.

Aspect 8: The ventilation system of aspect 7, wherein the first flow sensor is configured to measure an oxygen flow rate at which oxygen is provided from the oxygen source to the inlet opening of the mask body.

Aspect 9: The ventilation system of aspect 7, further comprising a second flow sensor that is positioned in operative communication with the processor and configured to measure an oxygen flow rate at which oxygen is provided from the oxygen source to the inlet opening of the mask body.

Aspect 10: The ventilation system of aspect 8, wherein the processor is configured to determine a fraction of inspired oxygen ($FiO_2$) value based upon the measured air and oxygen flow rates.

Aspect 11: The ventilation system of any one of the preceding aspects, wherein the processor is configured to generate a pressure alarm in response to the measured pressure in the mask falling below a predetermined value.

Aspect 12: The ventilation system of any one of the preceding aspects, wherein the processor is configured to selectively activate the blowing assembly to maintain a desired pressure within the mask.

Aspect 13: The ventilation system of aspect 8, wherein the processor is configured to calculate a leak flow rate according to the equation: Leak Flow Rate=Leak Factor×Mask Pressure, wherein Leak Flow Rate=the flow rate at which air exits the plurality of leak openings of the mask body; and Mask Pressure=the measured pressure within the mask.

Aspect 14: The ventilation system of aspect 13, wherein the processor is configured to determine a patient flow rate according to the equation: Patient Flow Rate=Total Flow Rate−Leak Flow Rate, wherein Patient Flow Rate=the flow rate of gas inhaled by a patient; and Total Flow Rate=the flow rate of gas supplied to the inlet opening of the mask body.

Aspect 15: The ventilation system of aspect 14, wherein the processor is configured to determine a respiratory rate of a subject based upon measured changes in the pressure within the mask body, and wherein the processor is configured to determine a tidal volume of each breath of the subject based upon the determined patient flow rate.

Aspect 16: The ventilation system of aspect 15, wherein the processor is configured to determine a Leak Factor for each respective breath of the subject.

Aspect 17: The ventilation system of aspect 15, wherein the processor is configured to produce an alarm in response to one or more of the following conditions: a tidal volume of the subject following below a predetermined volume; a respiratory rate of the subject following below a predetermined rate; a change in resistance within the lungs of the subject; an obstruction within the airway of the subject; and an excessive leak flow rate indicative of a disconnected mask.

Aspect 18: The ventilation system of any one of the preceding aspects, wherein the processor is configured to selectively activate the blowing assembly to deliver breaths to the subject by varying the pressure within the mask.

Aspect 19: The ventilation system of aspect 18, wherein the processor is configured to shift the ventilation system among a monitoring mode in which the blowing assembly does not actively deliver breaths to the subject and a pressure support mode in which the blowing assembly actively delivers breaths to the subject by varying the pressure within the mask.

Aspect 20: The ventilation system of aspect 19, wherein the processor is configured to automatically shift the ventilation system among the monitoring mode and the pressure support mode in response to changing conditions of the ventilation system or the subject.

Aspect 21: The ventilation system of any one of the preceding aspects, wherein the blowing assembly is configured to deliver air to the inlet opening of the mask body at a pressure of up to about 25 cm $H_2O$.

Aspect 22: The ventilation system of any one of the preceding aspects, wherein the blowing assembly and the processor are operatively associated with the mask, and wherein the ventilation system is portable.

Aspect 23: The ventilation system of aspect 22, wherein the ventilation system weighs less than 3 pounds.

Aspect 24: The ventilation system of aspect 22, wherein the ventilation system comprises a display device positioned in operative communication with the processor and configured to display information regarding one or more conditions of the ventilation system or a subject.

Aspect 25: The ventilation system of aspect 24, wherein the display device comprises a user interface.

Aspect 26: The ventilation system of any one of the preceding aspects, wherein the ventilation system does not comprise source of compressed gas.

Aspect 27: The ventilation system of any one of the preceding aspects, wherein the mask comprises a chin support assembly coupled to the mask body.

Aspect 28: The ventilation system of claim 22, wherein the ventilation system is configured for one-handed operation by a user.

Aspect 29: The ventilation system of aspect 14, wherein the processor is configured to generate a patient alarm in response to the patient flow rate falling below a predetermined value.

Aspect 30: A ventilation method comprising: using the ventilation system of any one of aspects 3-29.

All publications and patent applications mentioned in the specification (including the "References" section which follows) are indicative of the level of those skilled in the art to which this invention pertains. All publications and patent applications are herein incorporated by reference to the same extent as if each individual publication or patent application was specifically and individually indicated to be incorporated by reference.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

REFERENCES

1. American Society of Anesthesiologists Task Force on Sedation and Analgesia by Non-Anesthesiologists. Practice guidelines for sedation and analgesia by non-anesthesiologists. Anesthesiology 96, 1004-1017 (2002).
2. Wiesmann, W. P. The Dangers of Bag Valve Devices. Respiratory and Airway Management 1-3 (2012).

3. Sharma, V. K. et al. A national study of cardiopulmonary unplanned events after GI endoscopy. Gastrointestinal Endoscopy 66, 27-34 (2007).
4. Friedrich, K., Stremmel, W. & Sieg, A. Endoscopist-administered propofol sedation is safe—a prospective evaluation of 10,000 patients in an outpatient practice. J Gastrointestin Liver Dis 21, 259-263 (2012).
5. Pambianco, D. J., Whitten, C. J., Moerman, A., Struys, M. M. & Martin, J. F. An assessment of computer-assisted personalized sedation: a sedation delivery system to administer propofol for gastrointestinal endoscopy. Gastrointestinal Endoscopy 68, 542-547 (2008).
6. Dahan, A. Influence of anesthesia and analgesia on the control of breathing. British journal of anaesthesia 91, 40-49 (2003).
7. Persson, J. et al. Ketamine antagonises alfentanil-induced hypoventilation in healthy male volunteers. Acta Anaesthesiol Scand 43, 744-752 (1999).
8. Thornton, A. T., Singh, P., Ruehland, W. R. & Rochford, P. D. AASM criteria for scoring respiratory events: interaction between apnea sensor and hypopnea definition. Sleep 35, 425-432 (2012).
9. Cashman, J. N. Respiratory and haemodynamic effects of acute postoperative pain management: evidence from published data. British journal of anaesthesia 93, 212-223 (2004).
10. Ruehland, W. R. et al. The new AASM criteria for scoring hypopneas: impact on the apnea hypopnea index. Sleep 32, 150-157 (2009).
11. Dahan, A., Aarts, L. & Smith, T. W. Incidence, Reversal, and Prevention of Opioid-induced Respiratory Depression. Anesthesiology 112, 226-238 (2010).
12. Cole, P. J., Craske, D. A. & Wheatley, R. G. Efficacy and respiratory effects of low-dose spinal morphine for postoperative analgesia following knee arthroplasty. British journal of anaesthesia 85, 233-237 (2000).
13. Catley, D. M. et al. Pronounced, episodic oxygen desaturation in the postoperative period: its association with ventilatory pattern and analgesic regimen. Anesthesiology 63, 20-28 (1985).
14. Moser, N. J., Phillips, B. A., Berry, D. T. & Harbison, L. What is hypopnea, anyway? Chest 105, 426-428 (1994).
15. Xu, W. & Pan, Z. Definition of sleep apnea event by one minute HRV spectrum analysis. 2292-2294 (2008).
16. Stepnowsky, C., Zamora, T., Barker, R., Liu, L. & Sarmiento, K. Accuracy of Positive Airway Pressure Device—Measured Apneas and Hypopneas: Role in Treatment Followup. Sleep Disorders 2013, 1-6 (2013).
17. Ortega, R., Mehio, A. K., Woo, A. & Hafez, D. H. Positive-pressure ventilation with a face mask and a bag-valve device. The New England Journal of Medicine 357, (2007).
18. Rushing, J. Using Bag-Valve Mask Ventilation. Nursing 36, 1-2 (2006).
19. Airway & Council, V. M. W. G. O. T. E. R. Guidelines for the basic management of the airway and ventilation during resuscitation. A statement by the Airway and Ventilation Management Working Group of the European Resuscitation Council. Resuscitation 31, 187-200 (1996).
20. Airway & Council, V. M. W. G. O. T. E. R. Guidelines for the advanced management of the airway and ventilation during resuscitation. A statement by the Airway and Ventilation Management of the Working Group of the European Resuscitation Council. Resuscitation 31, 201-230 (1996).
21. Golzari, S. E. et al. Comparison of three methods in improving bag mask ventilation. Int J Prev Med 5, 489-493 (2014).
22. Smally, A. J., Ross, M. J. & Huot, C. P. Gastric rupture following bag-valve-mask ventilation. The Journal of Emergency Medicine 22, 27-29 (2002).
23. Dörges, V., Wenzel, V., Knacke, P. & Gerlach, K. Comparison of different airway management strategies to ventilate apneic, nonpreoxygenated patients. Critical care medicine 31, 800-804 (2003).
24. Meier, C. Airway management in patients with brain injury. Emerg Nurse 21, 18-23 (2013).
25. Shah, P. & Sundaram, V. Incidence and predictors of difficult mask ventilation and intubation, J Anaesthesiol Clin Pharmacol 28, 451 (2012).
26. Airway, A. S. O. A. T. F. O. M. O. T. D. Practice guidelines for management of the difficult airway. Anesthesiology 78, 597-602 (1993).
27. Brinker, A., Staffing, W. M. & Schumacher, J. Evaluation of bag-valve-mask ventilation in simulated toxic environments*. Anaesthesia 63, 1234-1237 (2008).
28. Gurajala, I., Azharuddin, M. & Gopinath, R. General anaesthesia with laryngeal mask airway may cause recurrence of pneumocephalus in a patient with head injury. British journal of anaesthesia 111, 675-676 (2013).
29. Soleimanpour, H. et al. Role of anesthesiology curriculum in improving bag-mask ventilation and intubation success rates of emergency medicine residents: a prospective descriptive study. BMC Emergency Medicine 11, 8 (2011).
30. Sollid, S. J., Heltne, J., Søreide, E. & Lossius, H. Pre-hospital advanced airway management by anaesthesiologists: Is there still room for improvement? Scand J Trauma Resusc Emerg Med 16, 2 (2008).
31. De Regge, M., Vogels, C., Monsieurs, K. G. & Calle, P. A. Retention of ventilation skills of emergency nurses after training with the SMART BAG® compared to a standard bag-valve-mask. Resuscitation 68, 379-384 (2006).
32. Verathon. Intubation Fact Sheet. (2005).
33. Carron, M., Freo, U., BaHammam, A. S. & al, E. Complications of non-invasive ventilation techniques: a comprehensive qualitative review of randomized trials. British journal of . . . (2013).
34. AutoMedx. AutoMedx SAVe II 510(k) Summary. FDA 1-16 (2014).
35. Nielsen, J. Enhancing the explanatory power of usability heuristics. Proceedings of the SIGCHI Conference on Human Factors in Computing Systems, 152-158 (1994)
36. Seeff, L. C. et al. How many endoscopies are performed for colorectal cancer screening? Results from CDC's survey of endoscopic capacity. Gastroenterology 127, 1670-1677 (2004).

What is claimed is:

1. A ventilation mask comprising:
  a mask body having an inner surface configured for engagement with a face of a subject and an opposed outer surface; and
  a pressure sensor operatively associated with the mask body and configured to measure pressure within the ventilation mask,
  wherein the mask body defines an inlet opening and a plurality of leak openings extending between the inner and outer surfaces of the mask body,
  wherein the openings of the plurality of leak openings are disposed around a peripheral edge of the mask body, are spaced about a peripheral face interface portion of the mask body, and are spaced apart so that the plurality of leak openings cannot be fully blocked when held by a hand of an operator, and wherein the inlet opening is configured to receive air from a blowing assembly.

2. The ventilation mask of claim 1, further comprising a chin support assembly coupled to the mask body, the chin support assembly comprising one or more straps configured to maintain a desired orientation of the subject.

3. A ventilation system comprising:
a mask comprising:
a mask body having an inner surface configured for engagement with a face of a subject and an opposed outer surface; and
a pressure sensor operatively associated with the mask body and configured to measure pressure within the mask,
wherein the mask body defines an inlet opening and a plurality of leak openings extending between the inner and outer surfaces of the mask body, and wherein the leak openings of the plurality of leak openings are disposed around a peripheral edge of the mask body, are spaced about a peripheral face interface portion of the mask body, and are spaced apart so that the plurality of leak openings cannot be fully blocked when held by a hand of an operator;
a blowing assembly positioned in fluid communication with the inlet opening of the mask body and configured to direct air to the inlet opening of the mask; and
a processor positioned in operative communication with the blowing assembly and the pressure sensor of the mask, wherein the processor is configured to selectively control the blowing assembly based upon at least the measured pressure within the mask.

4. The ventilation system of claim 3, further comprising a first flow sensor that is positioned in communication with the first processor and configured to measure an air flow rate at which air is provided from the blowing assembly to the inlet opening of the mask body.

5. The ventilation system of claim 4, further comprising an oxygen source positioned in fluid communication with the inlet opening of the mask body and configured to supply oxygen to the mask.

6. The ventilation system of claim 5, further comprising a second flow sensor configured to measure an oxygen flow rate at which oxygen is provided from the oxygen source to the inlet opening of the mask body.

7. The ventilation system of claim 6, wherein the processor is configured to determine a fraction of inspired oxygen (FiO2) value based upon a ratio of the measured air flow rate and the measured oxygen flow rate.

8. The ventilation system of claim 3, wherein the processor is configured to selectively activate the blowing assembly to maintain a desired pressure within the mask.

9. The ventilation system of claim 6, wherein the processor is configured to calculate a leak flow rate during a breath according to the equation:

$$\text{Leak Flow Rate} = \text{Leak Factor} \times \text{Mask Pressure},$$

wherein
Leak Flow Rate=the flow rate at which air exits the plurality of leak openings of the mask body; and
Mask Pressure=the measured pressure within the mask; and
Leak Factor=a calculated average of the air flow rate between breaths divided by the Mask Pressure between breaths.

10. The ventilation system of claim 9, wherein the processor is configured to determine a patient flow rate according to the equation:

$$\text{Patient Flow Rate} = \text{Total Flow Rate} - \text{Leak Flow Rate},$$

wherein
Patient Flow Rate=the flow rate of gas inhaled by a patient; and
Total Flow Rate=the flow rate of gas supplied to the inlet opening of the mask body.

11. The ventilation system of claim 10, wherein the processor is configured to determine a respiratory rate of a subject based upon measured changes in the pressure within the mask body, and wherein the processor is configured to determine a tidal volume of each breath of the subject based upon the determined patient flow rate.

12. The ventilation system of claim 10, wherein the processor is configured to determine the Leak Factor for each respective breath of the subject.

13. The ventilation system of claim 11, wherein the processor is configured to produce an alarm in response to one or more of the following conditions:
a tidal volume of the subject falling below a predetermined volume;
a respiratory rate of the subject falling below a predetermined rate;
a change in resistance within the lungs of the subject;
an obstruction within the airway of the subject;
an excessive leak flow rate indicative of a disconnected mask; and
pressure in the mask falling below a predetermined value.

14. The ventilation system of claim 3, wherein the processor is configured to detect apnea and, in response to the detection of apnea, selectively activate the blowing assembly to deliver breaths to the subject by varying the pressure within the mask.

15. The ventilation system of claim 14, wherein the processor is configured to shift the ventilation system among a monitoring mode in which the blowing assembly does not actively deliver breaths to the subject and a pressure support mode in which the blowing assembly actively delivers breaths to the subject by varying the pressure within the mask.

16. The ventilation system of claim 15, wherein the processor is configured to automatically shift the ventilation system among the monitoring mode and the pressure support mode in response to changing conditions of the ventilation system or the subject.

17. The ventilation system of claim 3, wherein the blowing assembly and the processor are operatively associated with the mask, and wherein the ventilation system is portable.

18. The ventilation system of claim 16, wherein the ventilation system comprises a display device positioned in operative communication with the processor and configured to display information regarding one or more conditions of the ventilation system or a subject, and wherein the display device comprises a user interface.

19. The ventilation system of claim 17, wherein the ventilation system is configured for one-handed operation by a user.

20. The ventilation system of claim 3, wherein the ventilation system does not comprise a source of compressed gas.

21. The ventilation system of claim 3, wherein the pressure sensor is positioned external to the mask body.

22. The ventilation system of claim 3, wherein the plurality of leak openings are positioned to prevent air from blowing directly into eyes of the subject.

23. The ventilation system of claim 3, wherein the peripheral face interface portion extends about an entirety of the mask body.

24. The ventilation system of claim 3, wherein the plurality of leak openings are oriented radially inward from the peripheral edge from about 1 mm to about 5 mm.

* * * * *